US008609730B2

(12) United States Patent
Chen et al.

(10) Patent No.: US 8,609,730 B2
(45) Date of Patent: Dec. 17, 2013

(54) REL INHIBITORS AND METHODS OF USE THEREOF

(75) Inventors: Youhai H. Chen, Newtown Square, PA (US); Ramachandran Murali, Swarthmore, PA (US); Jing Sun, Port Jefferson, NY (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 285 days.

(21) Appl. No.: 12/812,224

(22) PCT Filed: Jan. 7, 2009

(86) PCT No.: PCT/US2009/030325
§ 371 (c)(1), (2), (4) Date: Nov. 8, 2010

(87) PCT Pub. No.: WO2009/089277
PCT Pub. Date: Jul. 16, 2009

(65) Prior Publication Data
US 2011/0118325 A1     May 19, 2011

Related U.S. Application Data

(60) Provisional application No. 61/006,353, filed on Jan. 8, 2008, provisional application No. 61/071,374, filed on Apr. 24, 2008.

(51) Int. Cl.
*A61K 31/16* (2006.01)
(52) U.S. Cl.
USPC ............ 514/599; 514/825; 514/866; 514/903
(58) Field of Classification Search
USPC ................. 514/599, 903, 825, 866
See application file for complete search history.

(56) References Cited

U.S. PATENT DOCUMENTS

| 5,723,492 | A | 3/1998 | Chandrakumar et al. |
| 2004/0002513 | A1 | 1/2004 | Mazurov et al. |
| 2005/0137245 | A1 | 6/2005 | Hudkins et al. |
| 2006/0035979 | A1 | 2/2006 | Callahan et al. |
| 2007/0015809 | A1 | 1/2007 | Bressi et al. |
| 2007/0041981 | A1 | 2/2007 | Howard et al. |

FOREIGN PATENT DOCUMENTS

| WO | WO 2002/096888 | 12/2002 |
| WO | WO 2005/018557 | 3/2005 |
| WO | WO 2005/044786 | 5/2005 |
| WO | WO 2006/066133 | 6/2006 |
| WO | WO 2006/128129 A2 | 11/2006 |
| WO | WO 2007/005887 | 1/2007 |
| WO | WO 2007/007161 | 1/2007 |
| WO | WO 2007/075598 | 7/2007 |
| WO | WO 2007/075895 | 7/2007 |
| WO | WO 2007/120842 A2 | 10/2007 |
| WO | WO 2007/123953 | 11/2007 |
| WO | WO 2008/127615 | 10/2008 |
| WO | WO 2009/052319 | 4/2009 |

OTHER PUBLICATIONS

Cramer et al. Structure of the human NF-kB p52 homodimer-DNA complex at 2.1A resolution. The EMBO Journal 1997, vol. 16, pp. 7078, col. 2, para 3 and 4; p. 7079; Fig 1; p. 7086, Fig 58; 7080, Fig 2A.

*Primary Examiner* — Kevin E Weddington
(74) *Attorney, Agent, or Firm* — Mark S. Cohen; Pearl Cohen Zedek Latzer, LLP

(57) ABSTRACT

This invention provides REL inhibitors which interfere with the DNA binding capacity of a REL protein. Additionally this invention provides methods of treating, abrogating, or preventing diseases which respond with a positive clinical score to a REL inhibitor. Methods of identifying REL inhibitor based on a REL protein three dimensional model are described.

3 Claims, 5 Drawing Sheets

REL INHIBITORS AND METHODS OF USE THEREOF

CROSS-REFERENCE TO RELATED APPLICATIONS

This application is a National Phase Application of PCT International Application No. PCT/US09/30325, filed on Jan. 7, 2009, which claims the benefit of U.S. Provisional Application Ser. No. 61/006,353, filed Jan. 8, 2008 and U.S. Provisional Application Ser. No. 61/071,374, filed Apr. 24, 2008.

FIELD OF INVENTION

This invention provides REL inhibitors and methods of using and identifying the same. Specifically, the invention provides c-Rel inhibitors and their use in the treatment of Multiple Sclerosis.

BACKGROUND OF THE INVENTION

Experimental autoimmune encephalomyelitis (EAE) is an animal model for multiple sclerosis (MS). While the genetic and environmental factors that trigger MS vary, the common pathological outcome of the disease is the destruction of myelin-producing oligodendrocytes and their associated neuronal axons through a process called encephalomyelitis. Development of encephalomyelitis requires coordinated expression of a large number of genes that mediate the activation, migration and effector function of inflammatory cells (activated lymphoid and myeloid cells). These include genes that encode inflammatory cytokines, chemokines, and cytotoxic enzymes. Expression of these inflammatory genes is tightly regulated at the transcriptional level by specific transcription factors. Recent studies indicate that, c-Rel, the lymphoid member of the Rel/nuclear factor-κB (Rel/NF-κB) family, is a long sought-after transcriptional regulator of EAE. The mammalian Rel/NF-κB family consists of five members, each of which is endowed with a distinct set of function not shared by other members, although each member may also perform additional functions common to the family.

Thus, unlike other members that are ubiquitously expressed, c-Rel is preferentially expressed by inflammatory cells, and is involved in regulating a special subset of immune responses. c-Rel-deficient mice do not suffer from developmental problems or infectious diseases, but are resistant to inflammatory diseases (despite the normal expression of other Rel/NF-κ B proteins); c-Rel-deficient T cells are competent in survival and Th2 type responses but are severely compromised in their Th1 and Th17 type responses.

The Rel/NF-κB family of transcription factors represents one of the most attractive targets for anti-inflammatory therapy. Because Rel/NF-κB directly controls the expression of multiple inflammatory genes, its blockade is more effective for controlling inflammation than blocking one or a few downstream inflammatory genes or proteins. The first generation Rel/NF-κB drugs that block the entire Rel/NF-κB family have already been tested in both humans and animals. These include proteasome inhibitors (e.g., the FDA-approved PS-341), Rel/NF-κB decoy oligodeoxynucleotides and the NBD (nemo-binding domain) peptides, which are highly effective in preventing and treating models of autoimmune diseases including EAE. Additionally, glucocorticoids, which are currently used to control acute inflammation in MS patients, mediate their immunosuppressive effects, at least in part, through inhibiting Rel/NF-κB (glucocorticoids upregulate IKB expression and bind directly to Rel/NF-κB). However, because most Rel/NF-κB proteins are ubiquitously expressed and are involved in a variety of biological processes not related to autoimmunity, these drugs have significant side effects. Therefore, they can only be used for a short period of time to control acute inflammation.

SUMMARY OF THE INVENTION

This invention provides, a selective c-Rel inhibitor having the structure of formula (I):

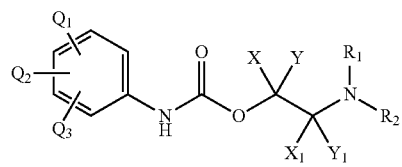

wherein $Q_1$, $Q_2$, $Q_3$ are independently H, halogen, $CF_3$, $OCH_2Ph$, O-alkyl, $OCF_3$, alkyl, or $Q_1$ and $Q_2$ form a saturated or unsaturated, substituted or unsubstituted, carbocyclic or heterocyclic ring with the aniline ring; X and Y are independently H, alkyl, or form a saturated or unsaturated, substituted or unsubstituted, carbocyclic or heterocyclic ring with $N(R_1)$ $(R_2)$.

$X_1$ and $Y_1$ are independently H, alkyl, or X and Y form together a double bond, or form saturated or unsaturated, substituted or un-substituted, carbocyclic or heterocyclic ring with $N(R_1)$ $(R_2)$.

$R_1$ and $R_2$ are independently H, $NH_2$, —N=alkyl, -alkyl, —$CH(Ph)_2$, substituted or un-substituted aryl, carbocyclic or heterocyclic aryl, substituted or un-substituted phenyl, C(O)-alkyl, or $R_1$ and $R_2$ form a saturated or unsaturated, substituted or un-substituted, carbocyclic or heterocyclic ring with the nitrogen atom;

or a selective c-Rel inhibitor having the structure of formula (II):

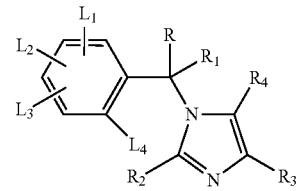

Wherein $L_1$, $L_2$, $L_3$ and $L_4$ are independently H, halogen, alkyl, —$NH_2$, —COO Alkyl, —$NO_2$, pyrrolidine, —O-alkyl, or $L_1$ and $L_2$ form a saturated or unsaturated, substituted or un-substituted, carbocyclic or heterocyclic fused ring with the benzene ring; or $L_4$ together with $R_2$ forms a 6 remembered fused ring with the imidazole and benzene rings;

R and $R_1$ are independently H, NHCO-alkyl, or form together a double bond (=), or CO group (=O);

$R_2$ is H, SH, OH, alkyl, -Ph-$CF_3$, —CH=C(Ph)-OC(O)-Ph, $CH_2$—S-Ph, $CH_2$—S-heterocyclic ring, $CH_2OC(O)NH$-Ph, —$NHCH_2CH_2OH$, -alkylene-OH, O-aryl, —O-alkyl, O—$CH_2$-Ph, O-phenyl, O-phenyl-alkyl, O-Ph-O-alkylene-Ph, —$OCH_2Ph$, —$OCH_2CH$=CHI-Ph, —S-Phenyl, NH-alkyl, NH-phenyl, NH-aryl, —N(Me)-alkylene-phenyl, —NH-alkylene-phenyl, —NH-alkylene-OMe, —NH—N=CH-Ph, —NH—N—C(O)-alkyl, —NH-heterocyclic ring, NH-carbocyclic ring, —C(O)Ph, substituted or un-substituted, saturated or unsaturated hetrocyclic ring, substituted or un-substituted, saturated or unsaturated carbocyclic ring, or $R_2$ together with $L_4$ forms a 6 membered fused ring with the imidazole and benzene rings;

$R_3$ is H, COO-alkyl, COOH, $NO_2$, substituted or un-substituted Ph, C(O)—N═NC(O)Ph or C(O)$NH_2$; and $R_4$ is H, Ph, alkyl, $NH_2$, OH, Ph-OH or $CH_2$—OH;

or a selective c-Rel inhibitor having the structure of formula (CXIX):

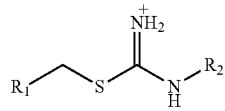

Wherein $R_1$ is substituted phenyl or unsubstituted phenyl, whereby a substituted phenyl ring comprises CN, halogen, or alkyl substituent;

$R_2$ is

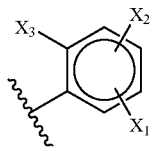

wherein $X_1$, $X_2$, or $X_3$ are independently H, halogen, alkyl, CN, COOH, or $NH_2$;

or $X_3$ forms with the ═$N^+H_2$ a five membered fused ring; or $R_2$ forms with ═$N^+H_2$ a five or six substituted or unsubstituted membered ring, whereby a five or six substituted membered ring comprises $CH_2$-Ph, aryl, or alkyl substituent.

In another embodiment, the present invention provides a composition comprising a selective c-Rel inhibitor having the structure of formula (I):

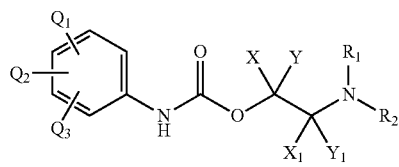

wherein $Q_1$, $Q_2$, $Q_3$ are independently H, halogen, $CF_3$, $OCH_2Ph$, O-alkyl, $OCF_3$, alkyl, or $Q_1$ and $Q_2$ form a saturated or unsaturated, substituted or un-substituted, carbocyclic or heterocyclic ring with the aniline ring;

X and Y are independently H, alkyl, or form a saturated or unsaturated, substituted or un-substituted, carbocyclic or heterocyclic ring with N($R_1$)($R_2$).

$X_1$ and $Y_1$ are independently H, alkyl, or X and Y form together a double bond, or form saturated or unsaturated, substituted or un-substituted, carbocyclic or heterocyclic ring with N($R_1$)($R_2$).

$R_1$ and $R_2$ are independently H, $NH_2$, —N═alkyl, -alkyl, —CH(Ph)$_2$, substituted or un-substituted aryl, carbocyclic or heterocyclic aryl, substituted or un-substituted phenyl, C(O)-alkyl, or $R_1$ and $R_2$ form a saturated or unsaturated, substituted or un-substituted, carbocyclic or heterocyclic ring with the nitrogen atom;

or a selective c-Rel inhibitor having the structure of formula (II):

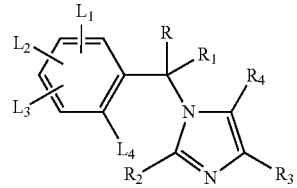

wherein $L_1$, $L_2$, $L_3$ and $L_4$ are independently H, halogen, alkyl, —$NH_2$, —COO Alkyl, —$NO_2$, pyrrolidine, —O-alkyl, or $L_1$ and $L_2$ form a saturated or unsaturated, substituted or un-substituted, carbocyclic or heterocyclic fused ring with the benzene ring; or $L_4$ together with $R_2$ forms a 6 membered fused ring with the imidazole and benzene rings;

R and $R_1$ are independently H, NHCO-alkyl, or form together a double bond (═), or CO group (═O);

$R_2$ is H, SH, OH, alkyl, -Ph-$CF_3$, —CH═C(Ph)-OC(O)-Ph, $CH_2$—S-Ph, $CH_2$—S-heterocyclic ring, $CH_2OC(O)NH$-Ph, —$NHCH_2CH_2OH$, -alkylene-OH, O-aryl, —O-alkyl, O—$CH_2$-Ph, O-phenyl, O-phenyl-alkyl, O-Ph-O-alkylene-Ph, —$OCH_2Ph$, —$OCH_2CH$═CH-Ph, —S-Phenyl, NH-alkyl, NH-phenyl, NH-aryl, —N(Me)-alkylene-phenyl, —NH-alkylene-phenyl, —NH-alkylene-OMe, —NH—N═CH-Ph, —NH—N—C(O)-alkyl, —NH-heterocyclic ring, NH-carbocyclic ring, —C(O)Ph, substituted or un-substituted, saturated or unsaturated hetrocyclic ring, substituted or un-substituted, saturated or unsaturated carbocyclic ring, or $R_2$ together with $L_4$ forms a 6 membered fused ring with the imidazole and benzene rings;

$R_3$ is H, COO-alkyl, COOH, $NO_2$, substituted or un-substituted Ph, C(O)—N═NC(O)Ph or C(O)$NH_2$; and;

R4 is H, Ph, alkyl, $NH_2$, OH, Ph-OH or $CH_2$—OH;

or a selective c-Rel inhibitor having the structure of formula (CXIX):

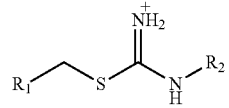

Wherein $R_1$ is substituted phenyl or unsubstituted phenyl, whereby a substituted phenyl ring comprises CN, halogen, or alkyl substituent;

$R_2$ is

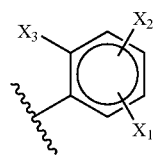

wherein $X_1$, $X_2$, or $X_3$ are independently H, halogen, alkyl, CN, COOH, or $NH_2$; or $X_3$ forms with the ═$N^+H_2$ a five membered fused ring; or $R_2$ forms with =$N^+H_2$ a five or six substituted or unsubstituted membered ring, whereby a five or six substituted membered ring comprises $CH_2$-Ph, aryl, or alkyl substituent.

In another embodiment, the present invention provides a method of treating multiple sclerosis, arthritis, diabetes, graft rejection, or a combination thereof in a subject comprising the step of contacting an inflammatory cell with a selective c-Rel inhibitor wherein the c-Rel inhibitor masks the L1 cavity of a c-Rel protein, thereby treating or preventing multiple sclerosis, arthritis, diabetes, graft rejection, or a combination thereof in a subject.

In one embodiment, the invention provides a method of inhibiting or suppressing the interaction between c-Rel and a DNA, comprising the step of contacting the c-Rel with a compound capable of masking the L1 cavity of the c-Rel, thereby inhibiting or suppressing the interaction between c-Rel and a DNA and inflammatory immune response.

In another embodiment, the present invention provides a method of preventing multiple sclerosis, arthritis, diabetes, graft rejection, or a combination thereof in a subject comprising the step of contacting an inflammatory cell with a selective c-Rel inhibitor wherein the c-Rel inhibitor masks the L1 cavity of a c-Rel protein, thereby treating or preventing multiple sclerosis, arthritis, diabetes, graft rejection, or a combination thereof in a subject.

In another embodiment, the present invention provides a method of inhibiting or suppressing multiple sclerosis, arthritis, diabetes, graft rejection, or a combination thereof in a subject comprising the step of contacting an inflammatory cell with a selective c-Rel inhibitor wherein the c-Rel inhibitor masks the L1 cavity of a c-Rel protein, thereby treating or preventing multiple sclerosis, arthritis, diabetes, graft rejection, or a combination thereof in a subject.

In another embodiment, the present invention provides a method of reducing the symptoms associated with multiple sclerosis, arthritis, diabetes, graft rejection, or a combination thereof in a subject comprising the step of contacting an inflammatory cell with a selective c-Rel inhibitor wherein the c-Rel inhibitor masks the L1 cavity of a c-Rel protein, thereby treating or preventing multiple sclerosis, arthritis, diabetes, graft rejection, or a combination thereof in a subject.

In another embodiment, the present invention provides a method of identifying a selective c-Rel inhibitor comprising the steps of: (a) constructing a c-Rel protein 3-D model; and (b) minimizing the model to said identify said selective c-Rel inhibitor, wherein said inhibitor interferes with L1 cavity, thereby identifying a selective c-Rel DNA binding inhibitor.

BRIEF DESCRIPTION OF THE FIGURES

FIG. 1A depicts a graph showing the IL-2 inhibitory effect of R13D (compound III), R13096 (compound CXX), and R13015 (compound VI). FIG. 1B depicts a graph showing the IFN-gamma inhibitory effect of R13D (compound III), R13096 (compound CXX), and R13015 (compound VI).

FIG. 2A depicts a surface model of c-Rel is shown in pale green color. The DNA binding region is shown in brown shadow. The L1 cavity, located between L1 and L2, is filled with an inhibitor shown in multiple colors. FIG. 2B depicts the inhibitor binding site together with the DNA (shown as a helix) binding site, as seen in the surface model of c-Rel, the inhibitor occupies the site where DNA binds. FIG. 2C is the chemical structure of the active inhibitor, R13D (compound III).

FIG. 4 shows a cell-based assay for testing c-Rel blockers. Splenocytes of C57BL/6 mice (n=4) were cultured with or without plate-bound anti-CD3 (1 ug/ml) and soluble anti-CD28 (2 ug/ml), in the presence of various concentrations of R96 as indicated. R96 was dissolved in PBS, and the amount of the PBS added to each culture was identical (5 ml per 200 ml culture). Twenty-four hours later, cytokines in the supernatant were determined by ELISA (A-C). The percentages of dead cells in the culture were determined by flow cytometry following staining cells with annexin-V and propidium iodide (PI)(D). No significant differences in the percentage of annexin-V+ and PI+ cells (dead cells) were observed among different cultures.

DETAILED DESCRIPTION OF THE INVENTION

Figure 1:
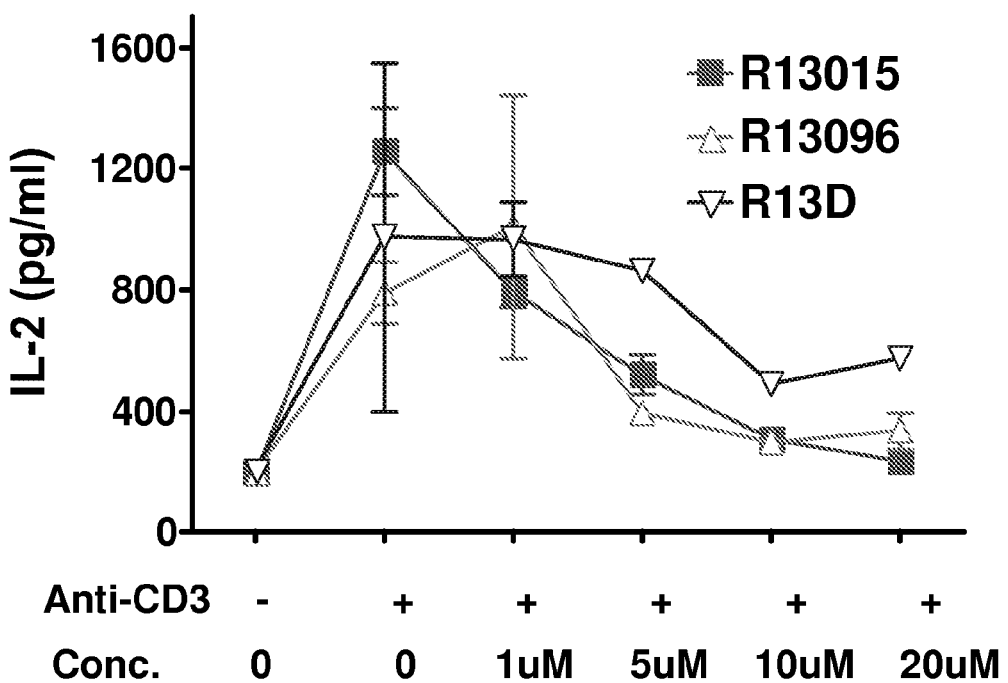
FIG. 1.
Figure 1:
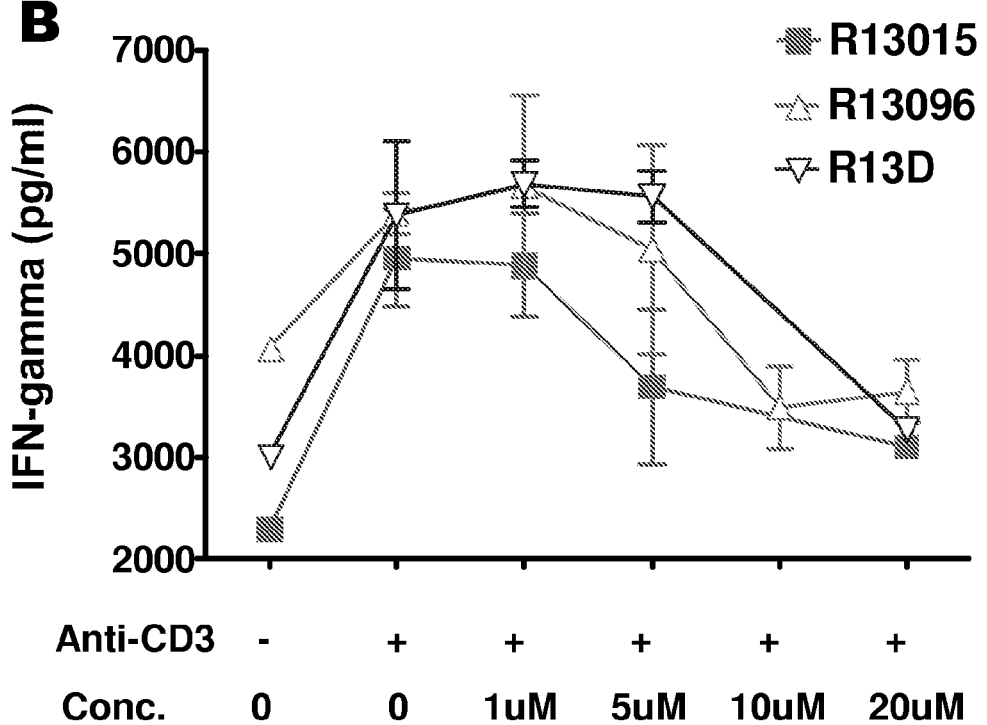

In one embodiment, provided herein are REL inhibitors and methods of using and identifying the same. In other embodiments, provided herein are c-Rel inhibitors and their use in the treatment of Multiple Sclerosis.

This invention provides a selective c-Rel inhibitor having the structure of formula (I)

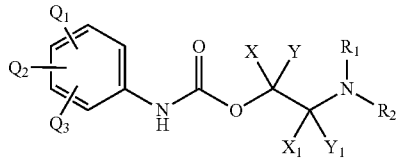

wherein $Q_1$, $Q_2$, $Q_3$ are independently H, halogen, $CF_3$, $OCH_2Ph$, O-alkyl, $OCF_3$, alkyl, or $Q_1$ and $Q_2$ form a saturated or unsaturated, substituted or un-substituted, carbocyclic or heterocyclic ring with the aniline ring; X and Y are independently H, alkyl, or form a saturated or unsaturated, substituted or un-substituted, carbocyclic or heterocyclic ring with $N(R_1)(R_2)$. $X_1$ and $Y_1$ are independently H, alkyl, or X and Y form together a double bond, or form saturated or unsaturated, substituted or un-substituted, carbocyclic or heterocyclic ring with $N(R_1)(R_2)$. $R_1$ and $R_2$ are independently H, $NH_2$, —N=alkyl, -alkyl, —$CH(Ph)_2$, substituted or un-substituted aryl, carbocyclic or heterocyclic aryl, substituted or un-substituted phenyl, C(O)-alkyl, or $R_1$ and $R_2$ form a saturated or unsaturated, substituted or un-substituted, carbocyclic or heterocyclic ring with the nitrogen atom;

or a selective c-Rel DNA binding inhibitor having the structure of formula (II):

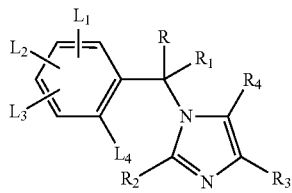

Wherein $L_1$, $L_2$, $L_3$ and $L_4$ are independently H, halogen, alkyl, —$NH_2$, —COOAlkyl, —$NO_2$, pyrrolidine, —O-alkyl, or $L_1$ and $L_2$ form a saturated or unsaturated, substituted or un-substituted, carbocyclic or heterocyclic fused ring with the benzene ring; or $L_4$ together with $R_2$ forms a 6 membered fused ring with the imidazole and benzene rings; R and $R_1$ are independently H, NHCO-alkyl, or form together a double bond (=), or CO group (=O); $R_2$ is H, SH, OH, alkyl, -Ph-$CF_3$, —CH=C(Ph)-OC(O)-Ph, $CH_2$—S-Ph, $CH_2$—S-heterocyclic ring, $CH_2OC(O)NH$-Ph, —$NHCH_2CH_2OH$, -alkylene-OH, O-aryl, —O-alkyl, O—$CH_2$-Ph, O-phenyl, O-phenyl-alkyl, O-Ph-O-alkylene-Ph, —$OCH_2Ph$, —$OCH_2CH$=CH-Ph, —S-Phenyl, NH-alkyl, NH-phenyl, NH-aryl, —N(Me)-alkylene-phenyl, —NH-alkylene-phenyl, —NH-alkylene-OMe, —NH—N=CH-Ph, —NH—N—C(O)-alkyl, —NH-heterocyclic ring, NH-carbocyclic ring, —C(O)Ph, substituted or un-substituted, saturated or unsaturated hetrocyclic ring, substituted or un-substituted, saturated or unsaturated carbocyclic ring, or $R_2$ together with $L_4$ forms a 6 membered fused ring with the imidazole and benzene rings; $R_3$ is H, COO-alkyl, COOH, $NO_2$, substituted or un-substituted Ph, C(O)—N=NC(O)Ph or C(O)$NH_2$; and; $R_4$ is H, Ph, alkyl, $NH_2$, OH, Ph-OH or $CH_2$—OH;

or a selective c-Rel DNA binding inhibitor having the structure of formula (CXIX):

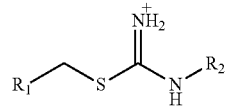

Wherein $R_1$ is substituted phenyl or unsubstituted phenyl, whereby a substituted phenyl ring comprises CN, halogen, or alkyl substituent;

$R_2$ is

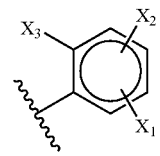

wherein $X_1$, $X_2$, or $X_3$ are independently H, halogen, alkyl, CN, COOH, or $NH_2$;

or $X_3$ forms with the =$N^+H_2$ a five membered fused ring; or $R_2$ forms with =$N^+H_2$ a five or six substituted or unsubstituted membered ring, whereby a five or six substituted membered ring comprises $CH_2$-Ph, aryl, or alkyl substituent.

Figure 2:
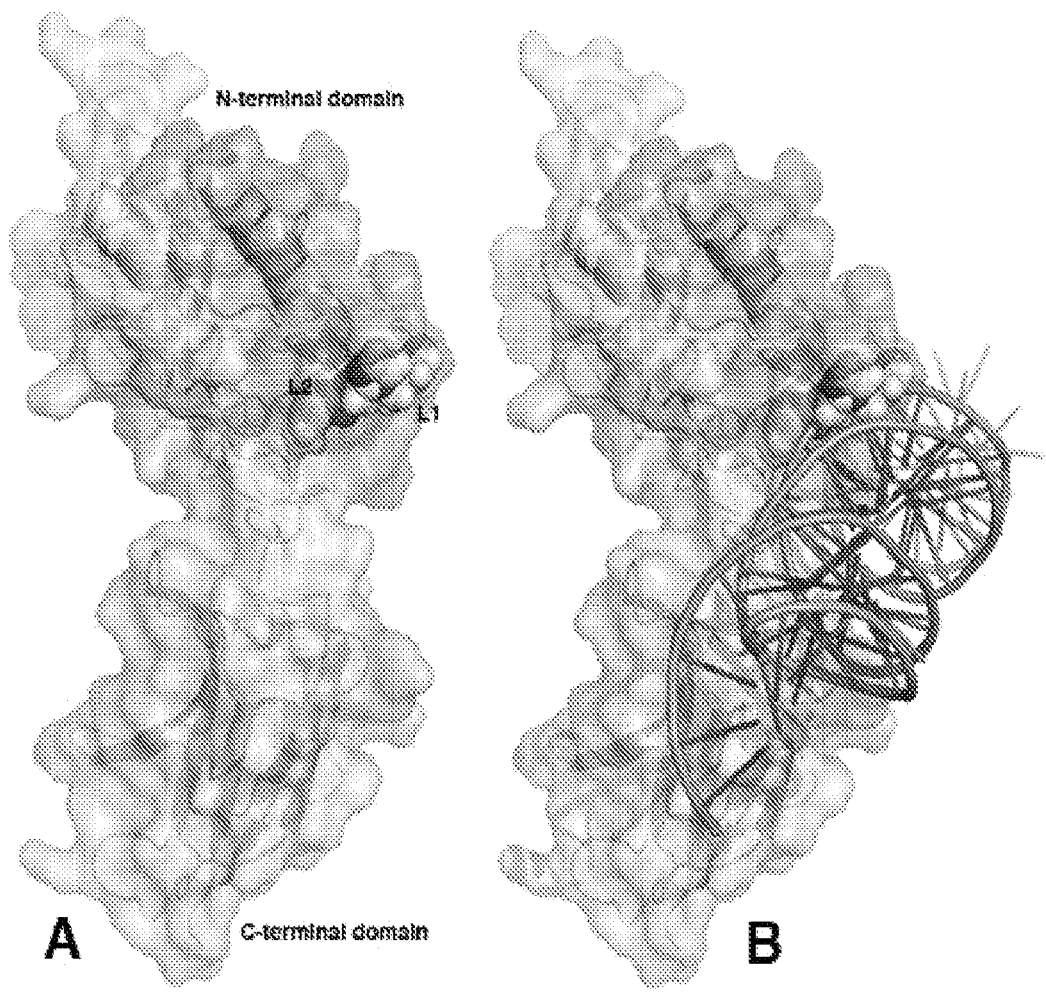
FIG. 2.

In another embodiment, the selective c-Rel inhibitor of the present invention blocks a druggable cavity. In another embodiment, the selective c-Rel DNA binding inhibitor of the present invention blocks a small druggable cavity. In another embodiment, the selective c-Rel DNA binding inhibitor of the present invention blocks the biological activity of c-Rel. In another embodiment, the selective c-Rel DNA binding inhibitor of the present invention interferes with the residues in loops L1 and L2 of the c-Rel protein (FIG. 2). In another embodiment, the selective c-Rel DNA binding inhibitor of the present invention comprises a c-Rel binding site. In another embodiment, upon binding of the selective c-Rel DNA binding inhibitor to c-Rel, the L1 cavity of the c-Rel protein is masked. In another embodiment, c-Rel:DNA contacts are mediated by four loops, L1 and L2 loops (FIG. 2A) from the N-terminal domain, and L3 and L4 loops from the C-terminal domain. In another embodiment, a DNA fragment is sandwiched between these loops.

In one embodiment, provided herein is a method of inhibiting or suppressing the interaction between c-Rel and a DNA, comprising the step of contacting the c-Rel with a compound capable of masking the L1 cavity of the c-Rel, thereby inhibiting or suppressing the interaction between c-Rel and a DNA and inflammatory immune response. In another embodiment, the compounds described herein are used in the methods of inhibiting or suppressing the interaction between c-Rel and DNA. In one embodiment, the compound capable of inhibiting the interaction between c-Rel and a DNA is the compound represented by the structure of formula III, also referred to in certain embodiments as R13:

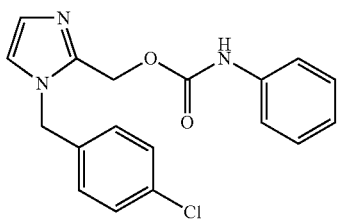 [SMILES: O=C(Nc1ccccc1)OCc1nccn1Cc1ccc(Cl)cc1]

or a pharmaceutical salt thereof; or in another embodiment, by the compound represented by the structure of formula CXX, also referred to interchangeably is compound 096 hereinbelow:

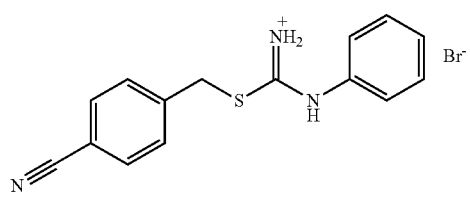 [SMILES: N#Cc1ccc(CSC(=N)Nc2ccccc2)cc1 ; [Br-]]

or a pharmaceutically acceptable salt thereof.

In another embodiment, the selective c-Rel DNA binding inhibitor of the present invention binds the L1 cavity formed by loops L1, L2 and a helix. In another embodiment, the L1 cavity comprises the AA Arg 21, Cys 26, Glu 27, Lys 110 and Lys 111. In another embodiment, the L1 cavity comprises the AA Arg 21 and Cys 26. In another embodiment, the L1 cavity comprises the AA Arg 21, Cys 26 and Glu 27. In another embodiment, the 1,l cavity comprises the AA Arg 21, Cys 26, Glu 27 and Lys 110. In another embodiment, the L1 cavity comprises the AA Arg 21, Cys 26, Glu 27, Lys 110 and Lys 111.

In another embodiment, the AA Arg 21, Cys 26, Glu 27, Lys 110 and Lys 111 form the mouth of the L1 cavity (FIG. 2). In another embodiment, the selective c-Rel DNA binding inhibitor of the present invention is screened for blocking the DNA binding to c-Rel. In another embodiment, the selective c-Rel DNA binding inhibitor of the present invention is screened for blocking the DNA binding to c-Rel by perturbing key contact residues in L1 loop.

In another embodiment, the inhibitor provided herein comprises the structure represented by formula III:

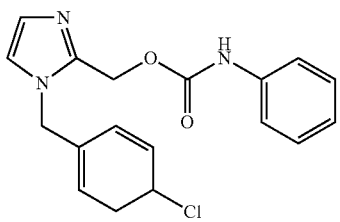 [SMILES: O=C(Nc1ccccc1)OCc1nccn1CC1=CCC(Cl)C=C1]

or its analog, metabolite or prodrug and their combination thereof.

In another embodiment, the inhibitor used in the compositions and methods provided, comprises the structure represented by formula IV:

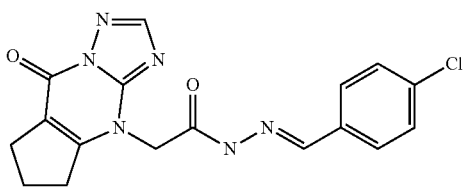 [SMILES: O=C(Cn1c2c(c(=O)n3ncnc13)CCC2)N/N=C/c1ccc(Cl)cc1]

or its analog, metabolite or prodrug and their combination thereof.

In another embodiment, the inhibitor used in the compositions and methods provided, comprises the structure represented by formula V:

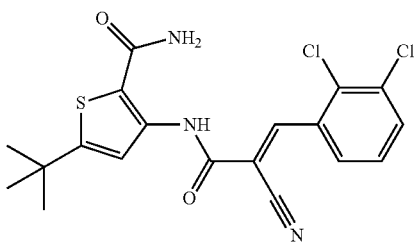 [SMILES: CC(C)(C)c1cc(NC(=O)/C(C#N)=C/c2cccc(Cl)c2Cl)c(C(N)=O)s1]

or its analog, metabolite or prodrug and their combination thereof.

In another embodiment, the inhibitor used in the compositions and methods provided, comprises the structure represented by formula VII:

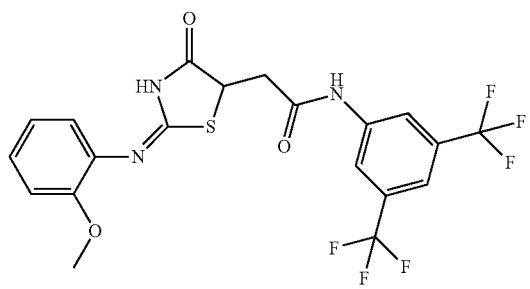 [SMILES: COc1ccccc1/N=C1\NC(=O)C(CC(=O)Nc2cc(C(F)(F)F)cc(C(F)(F)F)c2)S1]

or its analog, metabolite or prodrug and their combination thereof.

In another embodiment, the inhibitor used in the compositions and methods provided, comprises the structure represented by formula VIII:

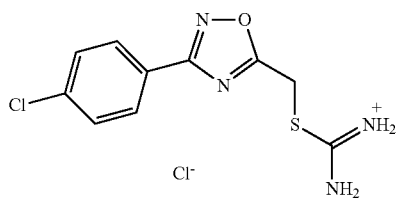

or its analog, metabolite or prodrug and their combination thereof.

In another embodiment, the inhibitor used in the compositions and methods provided, comprises the structure represented by formula IX:

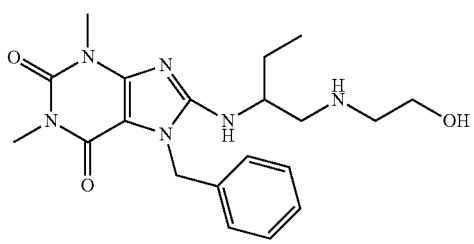 [SMILES: CCC(CNCCO)Nc1nc2c(c(=O)n(C)c(=O)n2C)n1Cc1ccccc1]

or its analog, metabolite or prodrug and their combination thereof.

In another embodiment, the inhibitor used in the compositions and methods provided, comprises the structure represented by formula X:

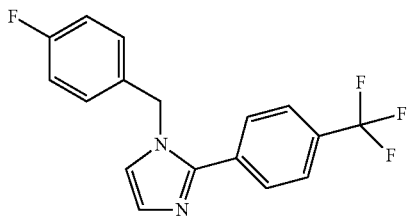 [SMILES: Fc1ccc(Cn2ccnc2-c2ccc(C(F)(F)F)cc2)cc1]

or its analog, metabolite or prodrug and their combination thereof.

In another embodiment, the inhibitor used in the compositions and methods provided, comprises the structure represented by formula XI:

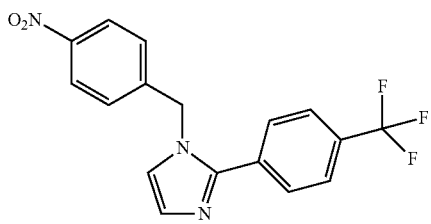 [SMILES: O=[N+]([O-])c1ccc(Cn2ccnc2-c2ccc(C(F)(F)F)cc2)cc1]

or its analog, metabolite or prodrug and their combination thereof.

In another embodiment, the inhibitor used in the compositions and methods provided, comprises the structure represented by formula XII:

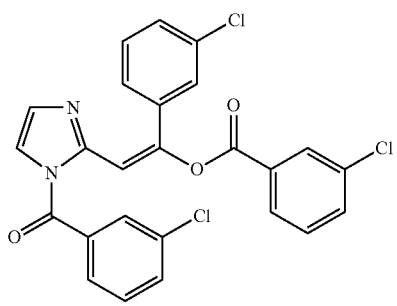 [SMILES: O=C(O/C(=C/c1nccn1C(=O)c1cccc(Cl)c1)c1cccc(Cl)c1)c1cccc(Cl)c1]

or its analog, metabolite or prodrug and their combination thereof.

In another embodiment, the inhibitor used in the compositions and methods provided, comprises the structure represented by formula XIII:

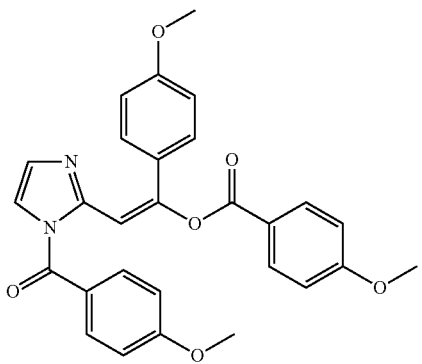 [SMILES: COc1ccc(C(=O)O/C(=C/c2nccn2C(=O)c2ccc(OC)cc2)c2ccc(OC)cc2)cc1]

or its analog, metabolite or prodrug and their combination thereof.

In another embodiment, the inhibitor used in the compositions and methods provided, comprises the structure represented by formula XIV:

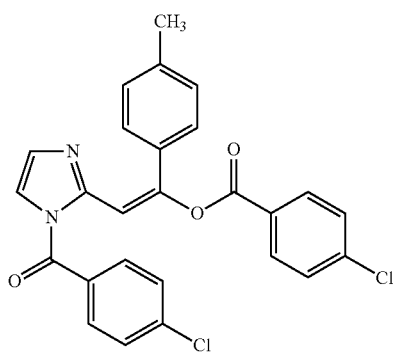 [SMILES: Cc1ccc(/C(=C\c2nccn2C(=O)c2ccc(Cl)cc2)OC(=O)c2ccc(Cl)cc2)cc1]

or its analog, metabolite or prodrug and their combination thereof.

In another embodiment, the inhibitor used in the compositions and methods provided, comprises the structure represented by formula XV:

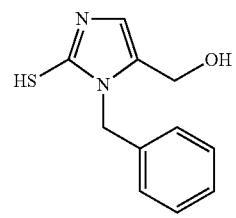 [SMILES: OCc1cnc(S)n1Cc1ccccc1]

or its analog, metabolite or prodrug and their combination thereof.

In another embodiment, the inhibitor used in the compositions and methods provided, comprises the structure represented by formula XVI:

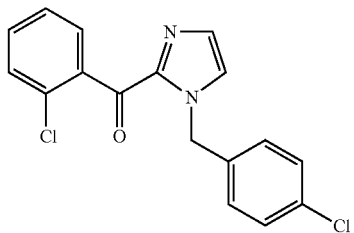 [SMILES: O=C(c1ccccc1Cl)c1nccn1Cc1ccc(Cl)cc1]

or its analog, metabolite or prodrug and their combination thereof.

In another embodiment, the inhibitor used in the compositions and methods provided, comprises the structure represented by formula XVII:

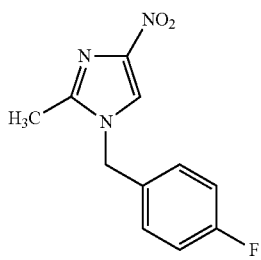 [SMILES: Cc1nc([N+](=O)[O-])cn1Cc1ccc(F)cc1]

or its analog, metabolite or prodrug and their combination thereof.

In another embodiment, the inhibitor used in the compositions and methods provided, comprises the structure represented by formula XVIII:

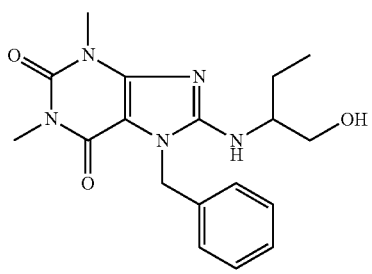 [SMILES: CCC(CO)Nc1nc2c(c(=O)n(C)c(=O)n2C)n1Cc1ccccc1]

or its analog, metabolite or prodrug and their combination thereof.

In another embodiment, the inhibitor used in the compositions and methods provided, comprises the structure represented by formula XIX:

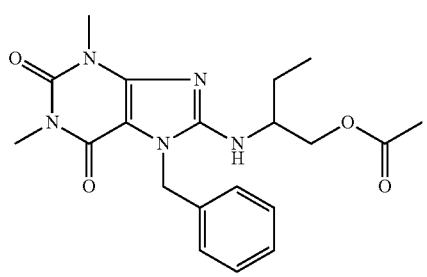 [SMILES: CCC(COC(C)=O)Nc1nc2c(c(=O)n(C)c(=O)n2C)n1Cc1ccccc1]

or its analog, metabolite or prodrug and their combination thereof.

In another embodiment, the inhibitor used in the compositions and methods provided, comprises the structure represented by formula XX:

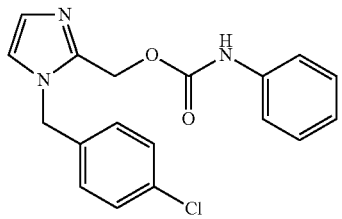 [SMILES: O=C(Nc1ccccc1)OCc1nccn1Cc1ccc(Cl)cc1]

or its analog, metabolite or prodrug and their combination thereof.

In another embodiment, the inhibitor used in the compositions and methods provided, comprises the structure represented by formula XXI:

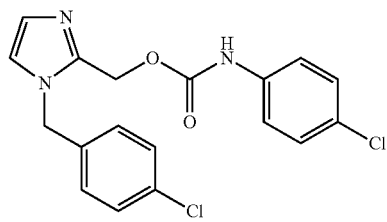 [SMILES: O=C(Nc1ccc(Cl)cc1)OCc1nccn1Cc1ccc(Cl)cc1]

or its analog, metabolite or prodrug and their combination thereof.

In another embodiment, the inhibitor used in the compositions and methods provided, comprises the structure represented by formula XXII:

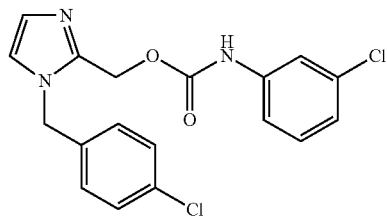 [SMILES: O=C(Nc1cccc(Cl)c1)OCc1nccn1Cc1ccc(Cl)cc1]

or its analog, metabolite or prodrug and their combination thereof.

In another embodiment, the inhibitor used in the compositions and methods provided, comprises the structure represented by formula XXIII:

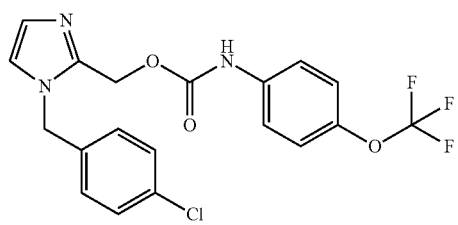 [SMILES: O=C(Nc1ccc(OC(F)(F)F)cc1)OCc1nccn1Cc1ccc(Cl)cc1]

or its analog, metabolite or prodrug and their combination thereof.

In another embodiment, the inhibitor used in the compositions and methods provided, comprises the structure represented by formula XXIV:

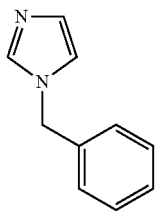 [SMILES: c1ccc(Cn2ccnc2)cc1]

or its analog, metabolite or prodrug and their combination thereof.

In another embodiment, the inhibitor used in the compositions and methods provided, comprises the structure represented by formula XXV:

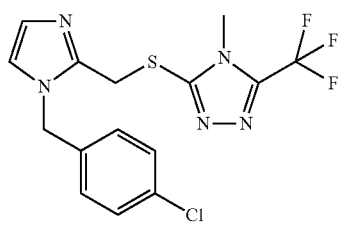 [SMILES: Cn1c(SCc2nccn2Cc2ccc(Cl)cc2)nnc1C(F)(F)F]

or its analog, metabolite or prodrug and their combination thereof.

In another embodiment, the inhibitor used in the compositions and methods provided, comprises the structure represented by formula XXVI:

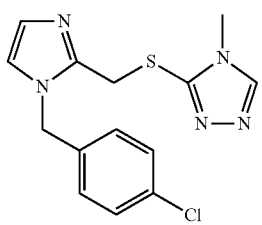 [SMILES: Cn1cnnc1SCc1nccn1Cc1ccc(Cl)cc1]

or its analog, metabolite or prodrug and their combination thereof.

In another embodiment, the inhibitor used in the compositions and methods provided, comprises the structure represented by formula XXVII:

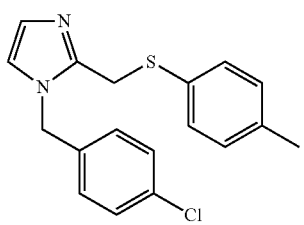 [SMILES: Cc1ccc(SCc2nccn2Cc2ccc(Cl)cc2)cc1]

or its analog, metabolite or prodrug and their combination thereof.

In another embodiment, the inhibitor used in the compositions and methods provided, comprises the structure represented by formula XXVII:

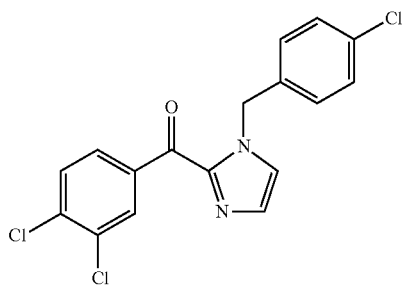 [SMILES: O=C(c1ccc(Cl)c(Cl)c1)c1nccn1Cc1ccc(Cl)cc1]

or its analog, metabolite or prodrug and their combination thereof.

In another embodiment, the inhibitor used in the compositions and methods provided, comprises the structure represented by formula XXIX:

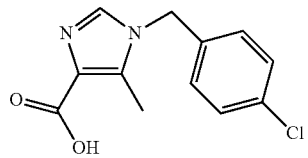 [SMILES: Cc1c(C(=O)O)ncn1Cc1ccc(Cl)cc1]

or its analog, metabolite or prodrug and their combination thereof.

In another embodiment, the inhibitor used in the compositions and methods provided, comprises the structure represented by formula XXX:

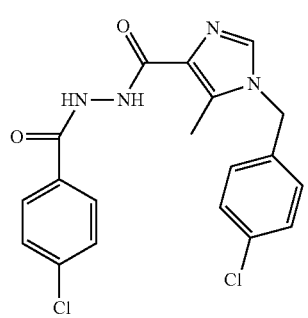 [SMILES: Cc1c(C(=O)NNC(=O)c2ccc(Cl)cc2)ncn1Cc1ccc(Cl)cc1]

or its analog, metabolite or prodrug and their combination thereof.

In another embodiment, the inhibitor used in the compositions and methods provided, comprises the structure represented by formula XXXI:

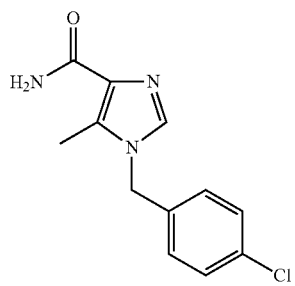 [SMILES: Cc1c(C(N)=O)ncn1Cc1ccc(Cl)cc1]

or its analog, metabolite or prodrug and their combination thereof.

In another embodiment, the inhibitor used in the compositions and methods provided, comprises the structure represented by formula XXXII:

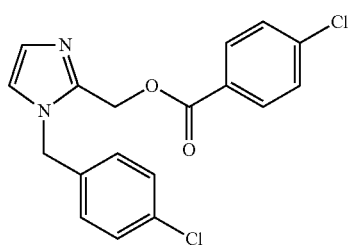 [SMILES: O=C(OCc1nccn1Cc1ccc(Cl)cc1)c1ccc(Cl)cc1]

or its analog, metabolite or prodrug and their combination thereof.

In another embodiment, the inhibitor used in the compositions and methods provided, comprises the structure represented by formula XXXIII:

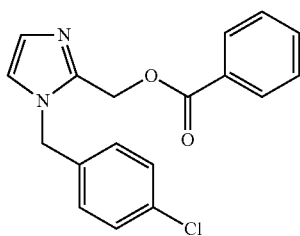 [SMILES: O=C(OCc1nccn1Cc1ccc(Cl)cc1)c1ccccc1]

or its analog, metabolite or prodrug and their combination thereof.

In another embodiment, the inhibitor used in the compositions and methods provided, comprises the structure represented by formula XXXIV:

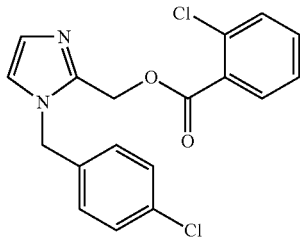 [SMILES: O=C(OCc1nccn1Cc1ccc(Cl)cc1)c1ccccc1Cl]

or its analog, metabolite or prodrug and their combination thereof.

In another embodiment, the inhibitor used in the compositions and methods provided, comprises the structure represented by formula XXXV:

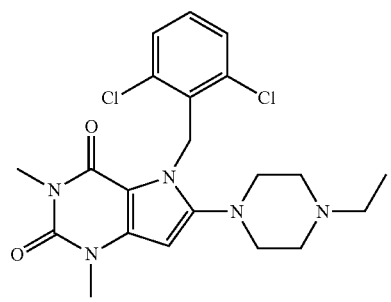 [SMILES: CCN1CCN(c2cc3c(c(=O)n(C)c(=O)n3C)n2Cc2c(Cl)cccc2Cl)CC1]

or its analog, metabolite or prodrug and their combination thereof.

In another embodiment, the inhibitor used in the compositions and methods provided, comprises the structure represented by formula XXXVI:

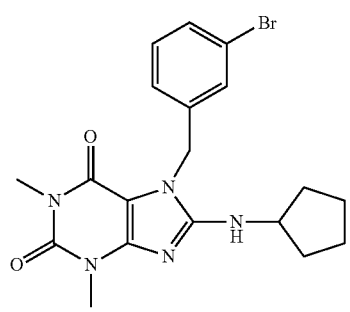 [SMILES: Cn1c(=O)c2c(nc(NC3CCCC3)n2Cc2cccc(Br)c2)n(C)c1=O]

or its analog, metabolite or prodrug and their combination thereof.

In another embodiment, the inhibitor used in the compositions and methods provided, comprises the structure represented by formula XXXVII:

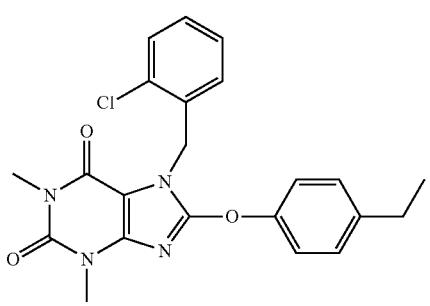 [SMILES: CCc1ccc(Oc2nc3c(c(=O)n(C)c(=O)n3C)n2Cc2ccccc2Cl)cc1]

or its analog, metabolite or prodrug and their combination thereof.

In another embodiment, the inhibitor used in the compositions and methods provided, comprises the structure represented by formula XXXVII:

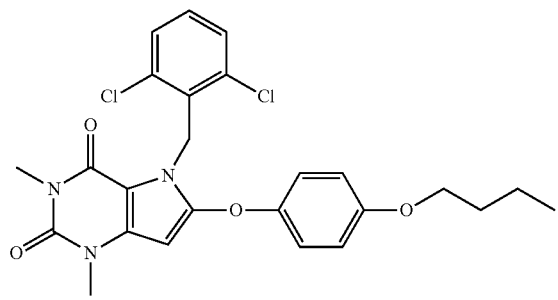 [SMILES: CCCCOc1ccc(Oc2cc3c(c(=O)n(C)c(=O)n3C)n2Cc2c(Cl)cccc2Cl)cc1]

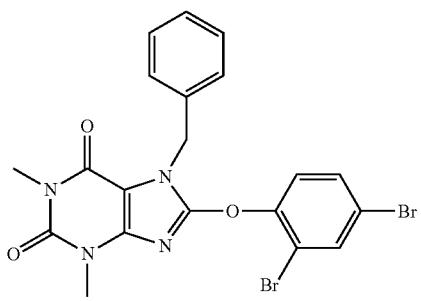

or its analog, metabolite or prodrug and their combination thereof.

In another embodiment, the inhibitor used in the compositions and methods provided, comprises the structure represented by formula XXXIX:

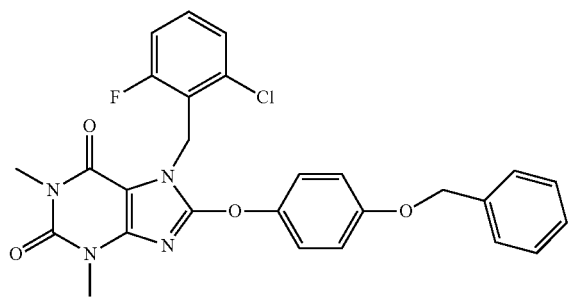 [SMILES: Cn1c(=O)c2c(nc(Oc3ccc(OCc4ccccc4)cc3)n2Cc2c(F)cccc2Cl)n(C)c1=O]

or its analog, metabolite or prodrug and their combination thereof.

In another embodiment, the inhibitor used in the compositions and methods provided, comprises the structure represented by formula XL:

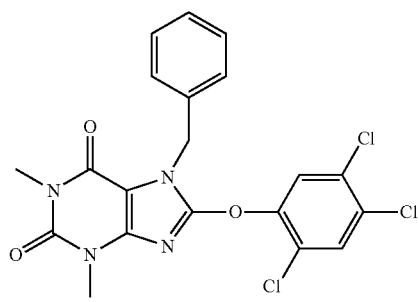 [SMILES: Cn1c(=O)c2c(nc(Oc3cc(Cl)c(Cl)cc3Cl)n2Cc2ccccc2)n(C)c1=O]

or its analog, metabolite or prodrug and their combination thereof.

In another embodiment, the inhibitor used in the compositions and methods provided, comprises the structure represented by formula XLI:

or its analog, metabolite or prodrug and their combination thereof.

In another embodiment, the inhibitor used in the compositions and methods provided, comprises the structure represented by formula XLII:

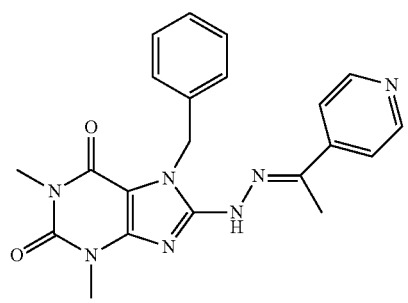 [SMILES: C/C(=N\Nc1nc2c(c(=O)n(C)c(=O)n2C)n1Cc1ccccc1)c1ccncc1]

or its analog, metabolite or prodrug and their combination thereof.

In another embodiment, the inhibitor used in the compositions and methods provided, comprises the structure represented by formula XLIII:

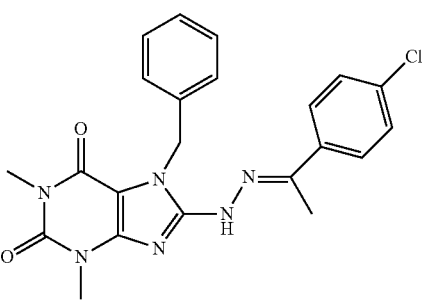 [SMILES: C/C(=N\Nc1nc2c(c(=O)n(C)c(=O)n2C)n1Cc1ccccc1)c1ccc(Cl)cc1]

or its analog, metabolite or prodrug and their combination thereof.

In another embodiment, the inhibitor used in the compositions and methods provided, comprises the structure represented by formula XLIV:

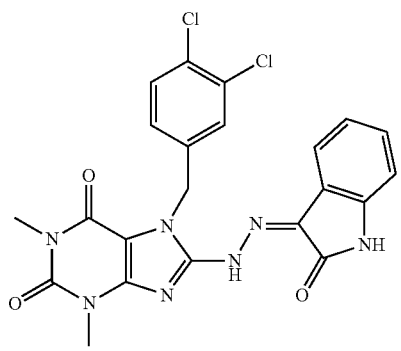 [SMILES: Cn1c(=O)c2c(nc(N/N=C3\C(=O)Nc4ccccc43)n2Cc2ccc(Cl)c(Cl)c2)n(C)c1=O]

or its analog, metabolite or prodrug and their combination thereof.

In another embodiment, the inhibitor used in the compositions and methods provided, comprises the structure represented by formula XLV:

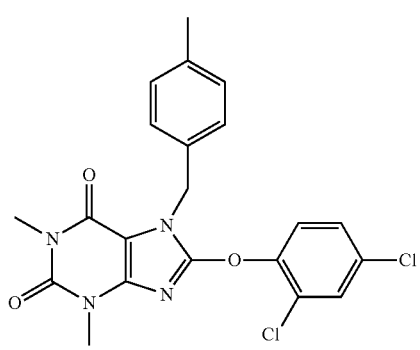 [SMILES: Cc1ccc(Cn2c(Oc3ccc(Cl)cc3Cl)nc3c2c(=O)n(C)c(=O)n3C)cc1]

or its analog, metabolite or prodrug and their combination thereof.

In another embodiment, the inhibitor used in the compositions and methods provided, comprises the structure represented by formula XLVI:

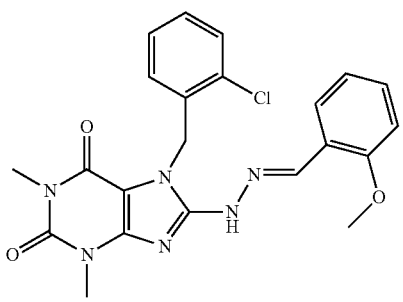 [SMILES: COc1ccccc1/C=N/Nc1nc2c(c(=O)n(C)c(=O)n2C)n1Cc1ccccc1Cl]

or its analog, metabolite or prodrug and their combination thereof.

In another embodiment, the inhibitor used in the compositions and methods provided, comprises the structure represented by formula XLVII

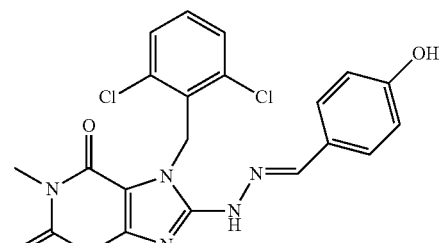

or its analog, metabolite or prodrug and their combination thereof.

In another embodiment, the inhibitor used in the compositions and methods provided, comprises the structure represented by formula XLVIII:

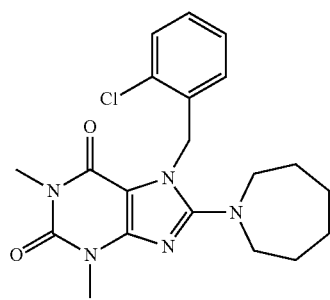 [SMILES: Cn1c(=O)c2c(nc(N3CCCCCC3)n2Cc2ccccc2Cl)n(C)c1=O]

or its analog, metabolite or prodrug and their combination thereof.

In another embodiment, the inhibitor used in the compositions and methods provided, comprises the structure represented by formula XLIX:

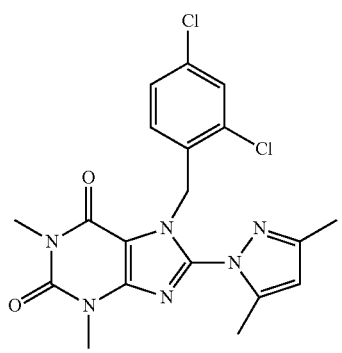 [SMILES: Cc1cc(C)n(-c2nc3c(c(=O)n(C)c(=O)n3C)n2Cc2ccc(Cl)cc2Cl)n1]

or its analog, metabolite or prodrug and their combination thereof.

In another embodiment, the inhibitor used in the compositions and methods provided, comprises the structure represented by formula L:

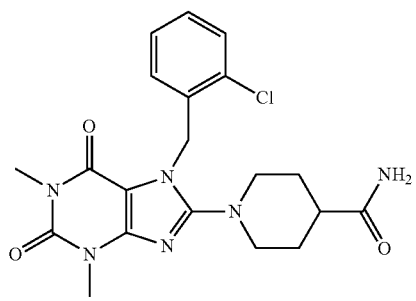 [SMILES: Cn1c(=O)c2c(nc(N3CCC(C(N)=O)CC3)n2Cc2ccccc2Cl)n(C)c1=O]

or its analog, metabolite or prodrug and their combination thereof.

In another embodiment, the inhibitor used in the compositions and methods provided, comprises the structure represented by formula LI:

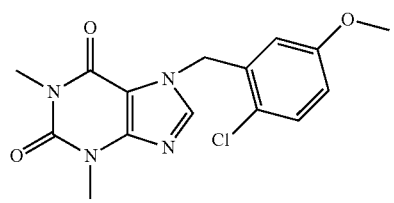

or its analog, metabolite or prodrug and their combination thereof.

In another embodiment, the inhibitor used in the compositions and methods provided, comprises the structure represented by formula LII:

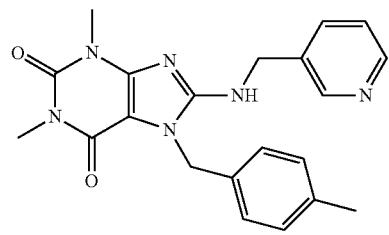 [SMILES: Cc1ccc(Cn2c(NCc3cccnc3)nc3c2c(=O)n(C)c(=O)n3C)cc1]

or its analog, metabolite or prodrug and their combination thereof.

In another embodiment, the inhibitor used in the compositions and methods provided, comprises the structure represented by formula LIII:

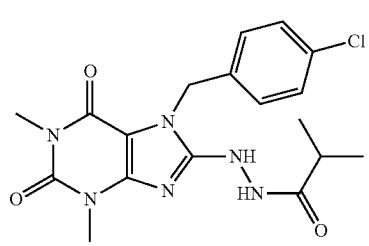 [SMILES: CC(C)C(=O)NNc1nc2c(c(=O)n(C)c(=O)n2C)n1Cc1ccc(Cl)cc1]

or its analog, metabolite or prodrug and their combination thereof.

In another embodiment, the inhibitor used in the compositions and methods provided, comprises the structure represented by formula LIV:

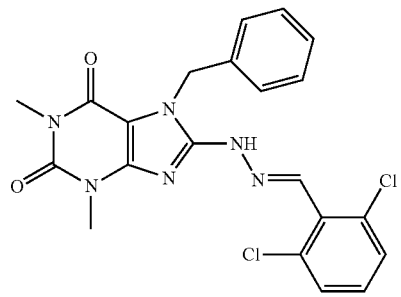 [SMILES: Cn1c(=O)c2c(nc(N/N=C/c3c(Cl)cccc3Cl)n2Cc2ccccc2)n(C)c1=O]

or its analog, metabolite or prodrug and their combination thereof.

In another embodiment, the inhibitor used in the compositions and methods provided, comprises the structure represented by formula LV:

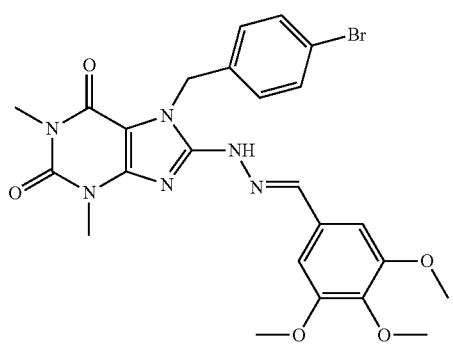

or its analog, metabolite or prodrug and their combination thereof.

In another embodiment, the inhibitor used in the compositions and methods provided, comprises the structure represented by formula LVI:

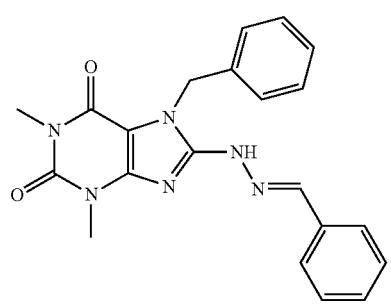 [SMILES: Cn1c(=O)c2c(nc(N/N=C/c3ccccc3)n2Cc2ccccc2)n(C)c1=O]

or its analog, metabolite or prodrug and their combination thereof.

In another embodiment, the inhibitor used in the compositions and methods provided, comprises the structure represented by formula LVII:

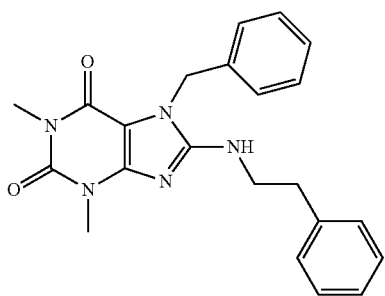 [SMILES: Cn1c(=O)c2c(nc(NCCc3ccccc3)n2Cc2ccccc2)n(C)c1=O]

or its analog, metabolite or prodrug and their combination thereof.

In another embodiment, the inhibitor used in the compositions and methods provided, comprises the structure represented by formula LVIII:

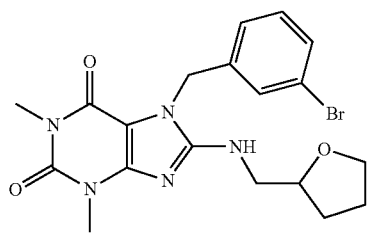 [SMILES: Cn1c(=O)c2c(nc(NCC3CCCO3)n2Cc2cccc(Br)c2)n(C)c1=O]

or its analog, metabolite or prodrug and their combination thereof.

In another embodiment, the inhibitor used in the compositions and methods provided, comprises the structure represented by formula LIX:

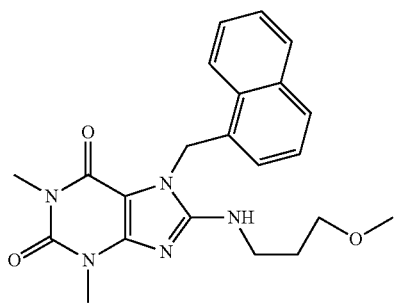

or its analog, metabolite or prodrug and their combination thereof.

In another embodiment, the inhibitor used in the compositions and methods provided, comprises the structure represented by formula LX:

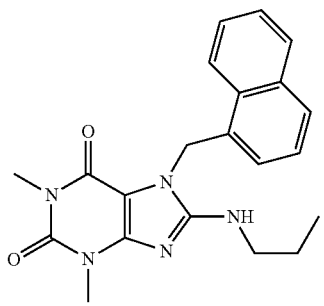 [SMILES: CCCNc1nc2c(c(=O)n(C)c(=O)n2C)n1Cc1cccc2ccccc12]

or its analog, metabolite or prodrug and their combination thereof.

In another embodiment, the inhibitor used in the compositions and methods provided, comprises the structure represented by formula LXI:

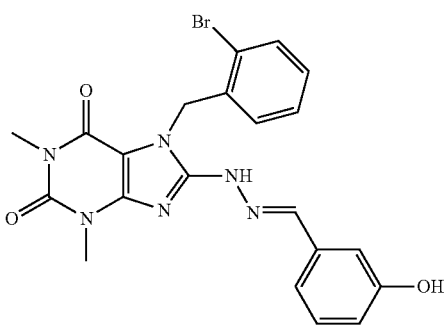 [SMILES: Cn1c(=O)c2c(nc(N/N=C/c3cccc(O)c3)n2Cc2ccccc2Br)n(C)c1=O]

or its analog, metabolite or prodrug and their combination thereof.

In another embodiment, the inhibitor used in the compositions and methods provided, comprises the structure represented by formula LXII:

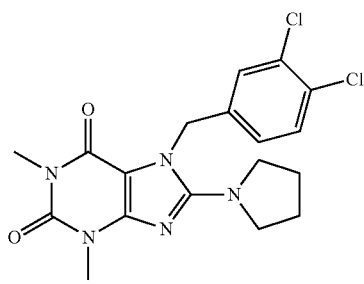 [SMILES: Cn1c(=O)c2c(nc(N3CCCC3)n2Cc2ccc(Cl)c(Cl)c2)n(C)c1=O]

or its analog, metabolite or prodrug and their combination thereof.

In another embodiment, the inhibitor used in the compositions and methods provided, comprises the structure represented by formula LXIII:

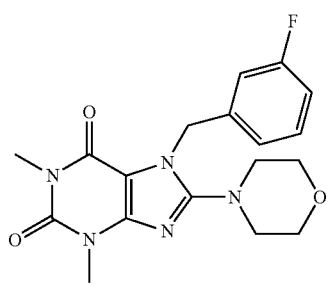 [SMILES: Cn1c(=O)c2c(nc(N3CCOCC3)n2Cc2cccc(F)c2)n(C)c1=O]

or its analog, metabolite or prodrug and their combination thereof.

In another embodiment, the inhibitor used in the compositions and methods provided, comprises the structure represented by formula LXIV:

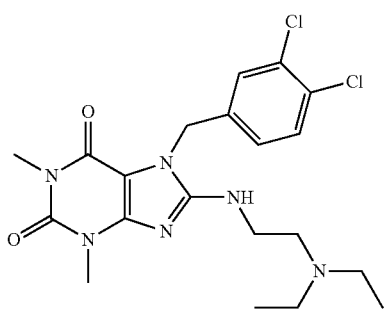 [SMILES: CCN(CC)CCNc1nc2c(c(=O)n(C)c(=O)n2C)n1Cc1ccc(Cl)c(Cl)c1]

or its analog, metabolite or prodrug and their combination thereof.

In another embodiment, the inhibitor used in the compositions and methods provided, comprises the structure represented by formula LXV:

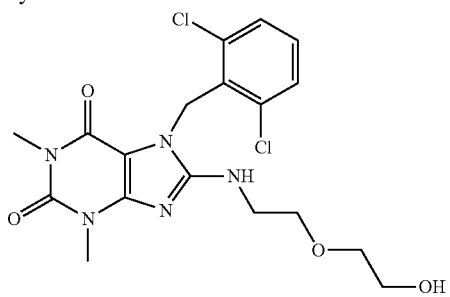

or its analog, metabolite or prodrug and their combination thereof.

In another embodiment, the inhibitor used in the compositions and methods provided, comprises the structure represented by formula LXVI

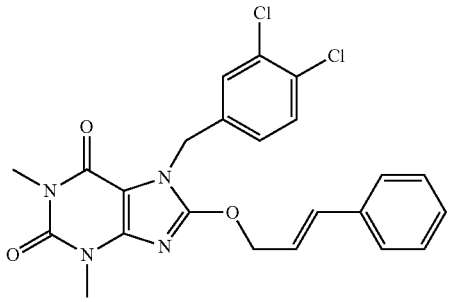 [SMILES: Cn1c(=O)c2c(nc(OC/C=C/c3ccccc3)n2Cc2ccc(Cl)c(Cl)c2)n(C)c1=O]

or its analog, metabolite or prodrug and their combination thereof.

In another embodiment, the inhibitor used in the compositions and methods provided, comprises the structure represented by formula LXVII:

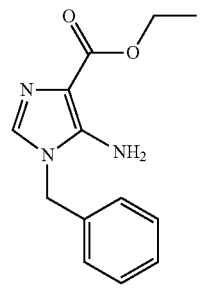 [SMILES: CCOC(=O)c1ncn(Cc2ccccc2)c1N]

or its analog, metabolite or prodrug and their combination thereof.

In another embodiment, the inhibitor used in the compositions and methods provided, comprises the structure represented by formula LXVIII:

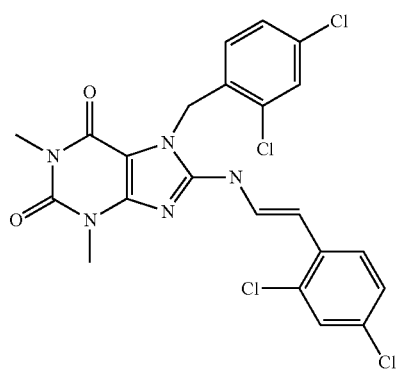 [SMILES: Cn1c(=O)c2c(nc(N/C=C/c3ccc(Cl)cc3Cl)n2Cc2ccc(Cl)cc2Cl)n(C)c1=O]

or its analog, metabolite or prodrug and their combination thereof.

In another embodiment, the inhibitor used in the compositions and methods provided, comprises the structure represented by formula LXIX:

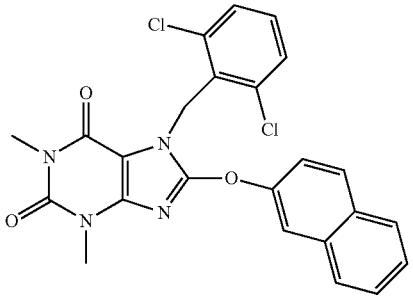 [SMILES: Cn1c(=O)c2c(nc(Oc3ccc4ccccc4c3)n2Cc2c(Cl)cccc2Cl)n(C)c1=O]

or its analog, metabolite or prodrug and their combination thereof.

In another embodiment, the inhibitor used in the compositions and methods provided, comprises the structure represented by formula LXX:

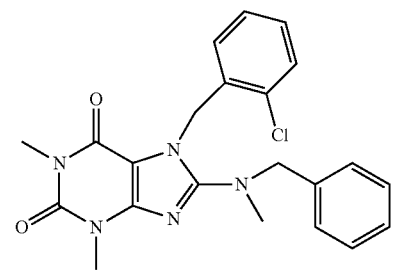 [SMILES: CN(Cc1ccccc1)c1nc2c(c(=O)n(C)c(=O)n2C)n1Cc1ccccc1Cl]

or its analog, metabolite or prodrug and their combination thereof.

In another embodiment, the inhibitor used in the compositions and methods provided, comprises the structure represented by formula LXXI:

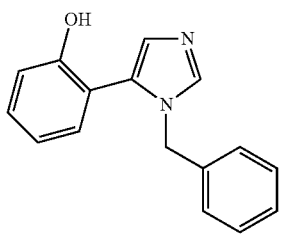 [SMILES: Oc1ccccc1-c1cncn1Cc1ccccc1]

or its analog, metabolite or prodrug and their combination thereof.

In another embodiment, the inhibitor used in the compositions and methods provided, comprises the structure represented by formula LXXII:

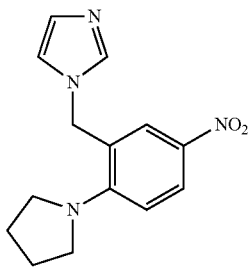 [SMILES: O=[N+]([O-])c1ccc(N2CCCC2)c(Cn2ccnc2)c1]

or its analog, metabolite or prodrug and their combination thereof.

In another embodiment, the inhibitor used in the compositions and methods provided, comprises the structure represented by formula LXXIII:

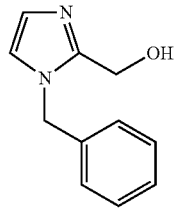 [SMILES: OCc1nccn1Cc1ccccc1]

or its analog, metabolite or prodrug and their combination thereof.

In another embodiment, the inhibitor used in the compositions and methods provided, comprises the structure represented by formula LXXIV:

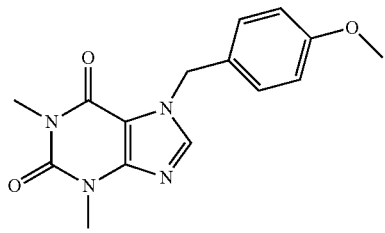 [SMILES: COc1ccc(Cn2cnc3c2c(=O)n(C)c(=O)n3C)cc1]

or its analog, metabolite or prodrug and their combination thereof.

In another embodiment, the inhibitor used in the compositions and methods provided, comprises the structure represented by formula LXXV:

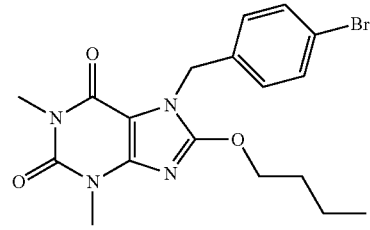 [SMILES: CCCCOc1nc2c(c(=O)n(C)c(=O)n2C)n1Cc1ccc(Br)cc1]

or its analog, metabolite or prodrug and their combination thereof.

In another embodiment, the inhibitor used in the compositions and methods provided, comprises the structure represented by formula LXXVI:

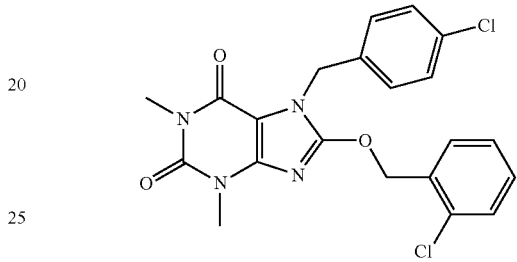

or its analog, metabolite or prodrug and their combination thereof.

In another embodiment, the inhibitor used in the compositions and methods provided, comprises the structure represented by formula LXXVII:

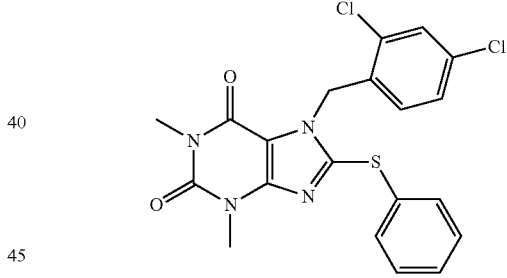

or its analog, metabolite or prodrug and their combination thereof.

In another embodiment, the inhibitor used in the compositions and methods provided, comprises the structure represented by formula LXXVIII:

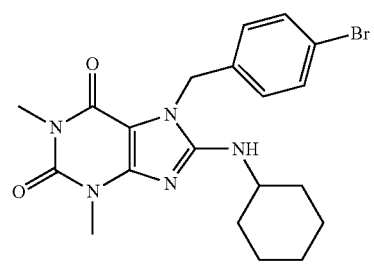 [SMILES: Cn1c(=O)c2c(nc(NC3CCCCC3)n2Cc2ccc(Br)cc2)n(C)c1=O]

or its analog, metabolite or prodrug and their combination thereof.

In another embodiment, the inhibitor used in the compositions and methods provided, comprises the structure represented by formula LXXIX:

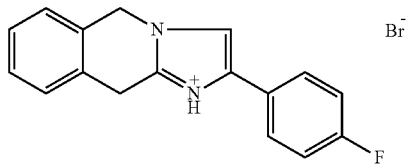

or its analog, metabolite or prodrug and their combination thereof.

In another embodiment, the inhibitor used in the compositions and methods provided, comprises the structure represented by formula LXXX:

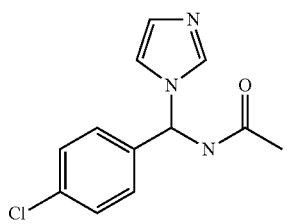 [SMILES: CC(=O)NC(c1ccc(Cl)cc1)n1ccnc1]

or its analog, metabolite or prodrug and their combination thereof.

In another embodiment, the inhibitor used in the compositions and methods provided, comprises the structure represented by formula LXXXI:

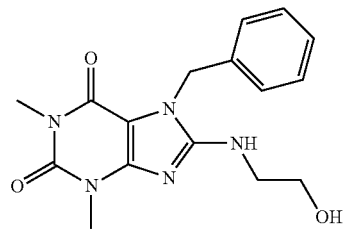 [SMILES: Cn1c(=O)c2c(nc(NCCO)n2Cc2ccccc2)n(C)c1=O]

or its analog, metabolite or prodrug and their combination thereof.

In another embodiment, the inhibitor used in the compositions and methods provided, comprises the structure represented by formula LXXXII:

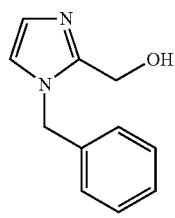 [SMILES: OCc1nccn1Cc1ccccc1]

or its analog, metabolite or prodrug and their combination thereof.

In another embodiment, the inhibitor used in the compositions and methods provided, comprises the structure represented by formula LXXXIII:

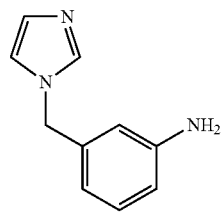 [SMILES: Nc1cccc(Cn2ccnc2)c1]

or its analog, metabolite or prodrug and their combination thereof.

In another embodiment, the inhibitor used in the compositions and methods provided, comprises the structure represented by formula LXXXIV:

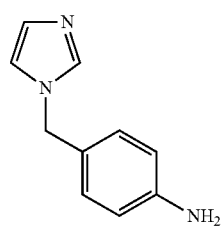 [SMILES: Nc1ccc(Cn2ccnc2)cc1]

or its analog, metabolite or prodrug and their combination thereof.

In another embodiment, the inhibitor used in the compositions and methods provided, comprises the structure represented by formula LXXV:

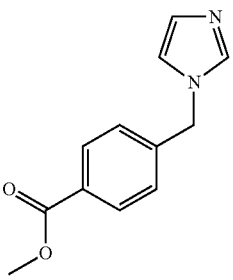 [SMILES: COC(=O)c1ccc(Cn2ccnc2)cc1]

or its analog, metabolite or prodrug and their combination thereof.

In another embodiment, the inhibitor used in the compositions and methods provided, comprises the structure represented by formula LXXXVI:

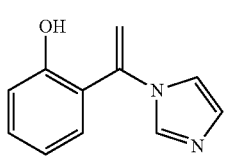

or its analog, metabolite or prodrug and their combination thereof.

In another embodiment, the inhibitor used in the compositions and methods provided, comprises the structure represented by formula LXXXVII:

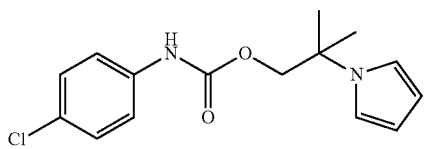 [SMILES: CC(C)(COC(=O)Nc1ccc(Cl)cc1)n1cccc1]

or its analog, metabolite or prodrug and their combination thereof.

In another embodiment, the inhibitor used in the compositions and methods provided, comprises the structure represented by formula LXXVIII:

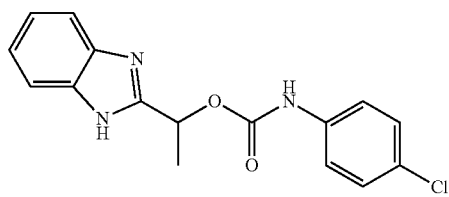 [SMILES: CC(OC(=O)Nc1ccc(Cl)cc1)c1nc2ccccc2[nH]1]

or its analog, metabolite or prodrug and their combination thereof.

In another embodiment, the inhibitor used in the compositions and methods provided, comprises the structure represented by formula LXXXIX:

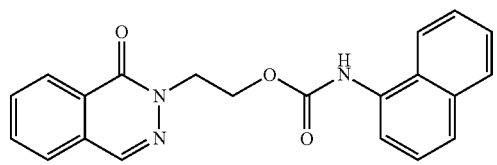 [SMILES: O=C(Nc1cccc2ccccc12)OCCn1ncc2ccccc2c1=O]

or its analog, metabolite or prodrug and their combination thereof.

In another embodiment, the inhibitor used in the compositions and methods provided, comprises the structure represented by formula XC:

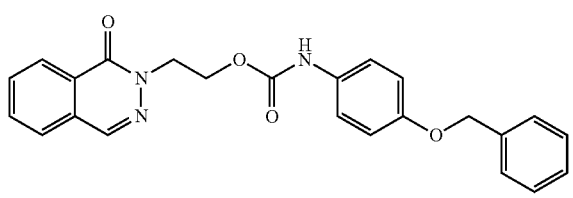 [SMILES: O=C(Nc1ccc(OCc2ccccc2)cc1)OCCn1ncc2ccccc2c1=O]

or its analog, metabolite or prodrug and their combination thereof.

In another embodiment, the inhibitor used in the compositions and methods provided, comprises the structure represented by formula XCI:

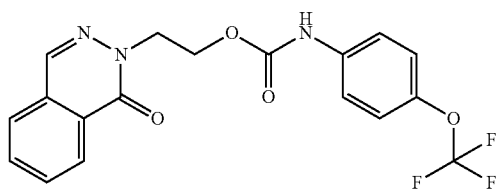 [SMILES: O=C(Nc1ccc(OC(F)(F)F)cc1)OCCn1ncc2ccccc2c1=O]

or its analog, metabolite or prodrug and their combination thereof.

In another embodiment, the inhibitor used in the compositions and methods provided, comprises the structure represented by formula XCII:

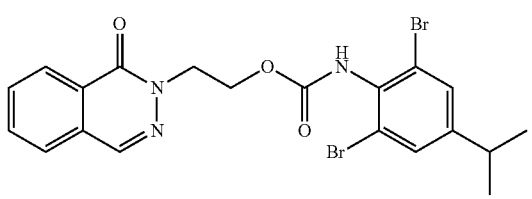 [SMILES: CC(C)c1cc(Br)c(NC(=O)OCCn2ncc3ccccc3c2=O)c(Br)c1]

or its analog, metabolite or prodrug and their combination thereof.

In another embodiment, the inhibitor used in the compositions and methods provided, comprises the structure represented by formula XCIII:

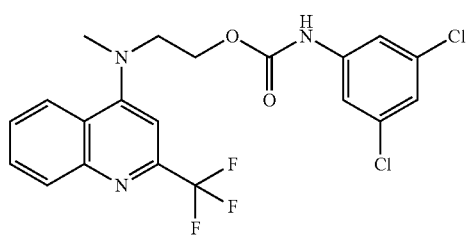 [SMILES: CN(CCOC(=O)Nc1cc(Cl)cc(Cl)c1)c1cc(C(F)(F)F)nc2ccccc12]

or its analog, metabolite or prodrug and their combination thereof.

In another embodiment, the inhibitor used in the compositions and methods provided, comprises the structure represented by formula XCIV:

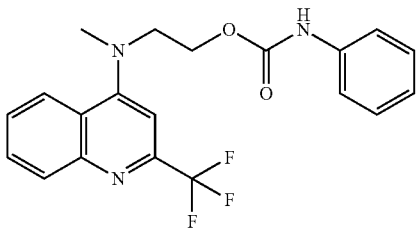 [SMILES: CN(CCOC(=O)Nc1ccccc1)c1cc(C(F)(F)F)nc2ccccc12]

or its analog, metabolite or prodrug and their combination thereof.

In another embodiment, the inhibitor used in the compositions and methods provided, comprises the structure represented by formula XCV:

[Structure of formula XCV]

or its analog, metabolite or prodrug and their combination thereof.

In another embodiment, the inhibitor used in the compositions and methods provided, comprises the structure represented by formula XCVI:

[Structure of formula XCVI]

or its analog, metabolite or prodrug and their combination thereof.

In another embodiment, the inhibitor used in the compositions and methods provided, comprises the structure represented by formula XCVII:

[Structure of formula XCVII]

or its analog, metabolite or prodrug and their combination thereof.

In another embodiment, the inhibitor used in the compositions and methods provided, comprises the structure represented by formula XCVIII:

[Structure of formula XCVIII]

or its analog, metabolite or prodrug and their combination thereof.

In another embodiment, the inhibitor used in the compositions and methods provided, comprises the structure represented by formula XCIX:

[Structure of formula XCIX]

or its analog, metabolite or prodrug and their combination thereof.

In another embodiment, the inhibitor used in the compositions and methods provided, comprises the structure represented by formula C:

[Structure of formula C]

or its analog, metabolite or prodrug and their combination thereof.

In another embodiment, the inhibitor used in the compositions and methods provided, comprises the structure represented by formula CI:

[Structure of formula CI]

or its analog, metabolite or prodrug and their combination thereof.

In another embodiment, the inhibitor used in the compositions and methods provided, comprises the structure represented by formula CII:

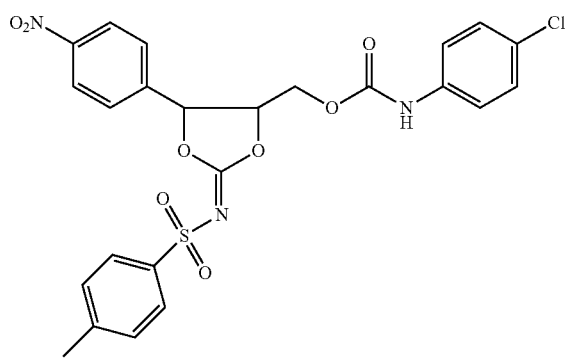 [SMILES: Cc1ccc(S(=O)(=O)/N=C2/OC(COC(=O)Nc3ccc(Cl)cc3)C(c3ccc([N+](=O)[O-])cc3)O2)cc1]

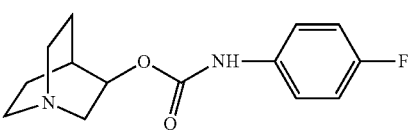

or its analog, metabolite or prodrug and their combination thereof.

In another embodiment, the inhibitor used in the compositions and methods provided, comprises the structure represented by formula CIII:

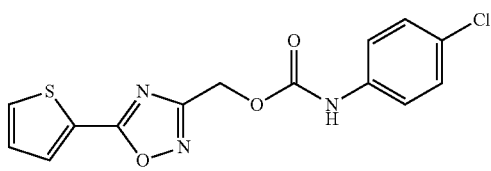 [SMILES: O=C(Nc1ccc(Cl)cc1)OCc1noc(-c2cccs2)n1]

or its analog, metabolite or prodrug and their combination thereof.

In another embodiment, the inhibitor used in the compositions and methods provided, comprises the structure represented by formula CIV:

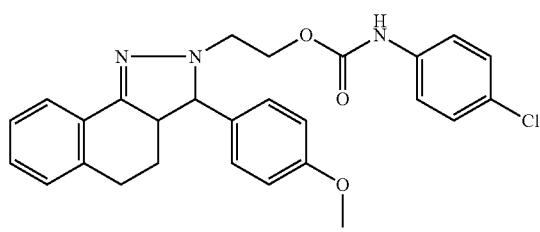 [SMILES: COc1ccc(C2C3CCc4ccccc4C3=NN2CCOC(=O)Nc2ccc(Cl)cc2)cc1]

or its analog, metabolite or prodrug and their combination thereof.

In another embodiment, the inhibitor used in the compositions and methods provided, comprises the structure represented by formula CV:

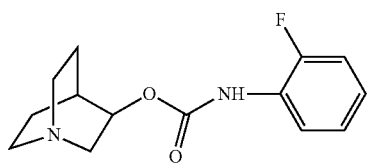

or its analog, metabolite or prodrug and their combination thereof.

In another embodiment, the inhibitor used in the compositions and methods provided, comprises the structure represented by formula CVI:

or its analog, metabolite or prodrug and their combination thereof.

In another embodiment, the inhibitor used in the compositions and methods provided, comprises the structure represented by formula CVII:

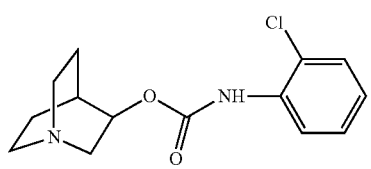 [SMILES: O=C(Nc1ccccc1F)OC1CN2CCC1CC2]

or its analog, metabolite or prodrug and their combination thereof.

In another embodiment, the inhibitor used in the compositions and methods provided, comprises the structure represented by formula CVIII:

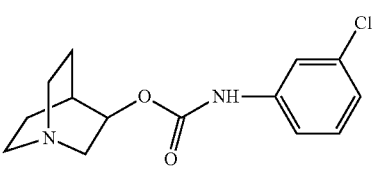 [SMILES: O=C(Nc1cccc(Cl)c1)OC1CN2CCC1CC2]

or its analog, metabolite or prodrug and their combination thereof.

In another embodiment, the inhibitor used in the compositions and methods provided, comprises the structure represented by formula CIX:

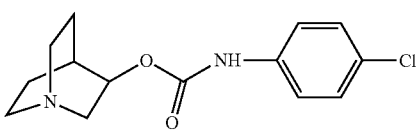 [SMILES: O=C(Nc1ccc(Cl)cc1)OC1CN2CCC1CC2]

or its analog, metabolite or prodrug and their combination thereof.

In another embodiment, the inhibitor used in the compositions and methods provided, comprises the structure represented by formula CX:

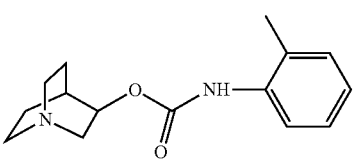 [SMILES: Cc1ccccc1NC(=O)OC1CN2CCC1CC2]

or its analog, metabolite or prodrug and their combination thereof.

In another embodiment, the inhibitor used in the compositions and methods provided, comprises the structure represented by formula CXI:

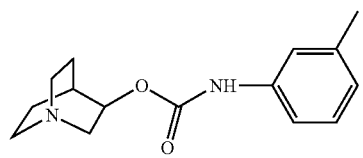 [SMILES: Cc1cccc(NC(=O)OC2CN3CCC2CC3)c1]

or its analog, metabolite or prodrug and their combination thereof.

In another embodiment, the inhibitor used in the compositions and methods provided, comprises the structure represented by formula CXII:

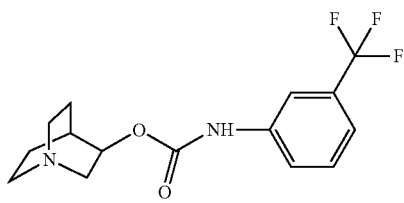 [SMILES: O=C(Nc1cccc(C(F)(F)F)c1)OC1CN2CCC1CC2]

or its analog, metabolite or prodrug and their combination thereof.

In another embodiment, the inhibitor used in the compositions and methods provided, comprises the structure represented by formula CXIII:

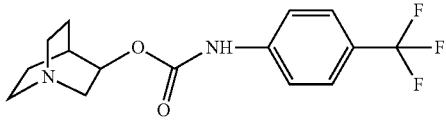 [SMILES: O=C(Nc1ccc(C(F)(F)F)cc1)OC1CN2CCC1CC2]

or its analog, metabolite or prodrug and their combination thereof.

In another embodiment, the inhibitor used in the compositions and methods provided, comprises the structure represented by formula CXIV:

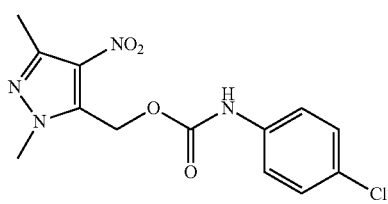 [SMILES: Cc1nn(C)c(COC(=O)Nc2ccc(Cl)cc2)c1[N+](=O)[O-]]

or its analog, metabolite or prodrug and their combination thereof.

In another embodiment, the inhibitor used in the compositions and methods provided, comprises the structure represented by formula CXV:

or its analog, metabolite or prodrug and their combination thereof.

In another embodiment, the inhibitor used in the compositions and methods provided, comprises the structure represented by formula CXVI:

or its analog, metabolite or prodrug and their combination thereof.

In another embodiment, the inhibitor used in the compositions and methods provided, comprises the structure represented by formula CXVII:

or its analog, metabolite or prodrug and their combination thereof.

In another embodiment, the inhibitor used in the compositions and methods provided, comprises the structure represented by formula CXVIII:

or its analog, metabolite or prodrug and their combination thereof.

In another embodiment, the inhibitor used in the compositions and methods provided, comprises the structure represented by formula CXIX

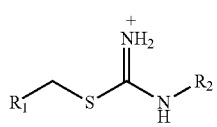

Wherein $R_1$ is substituted phenyl or unsubstituted phenyl, whereby a substituted phenyl ring comprises CN, halogen, or alkyl substituent;

$R_2$ is

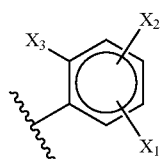

wherein $X_1$, $X_2$, or $X_3$ are independently H, halogen, alkyl, CN, COOH, or $NH_2$;

or $X_3$ forms with the $=N^+H_2$ a five membered fused ring $R_2$ forms with $=N^+H_2$ a five or six substituted or unsubstituted membered ring, whereby a five or six substituted membered ring comprises $CH_2$-Ph, aryl, or alkyl substituent.

In another embodiment, the inhibitor used in the compositions and methods provided, comprises the structure represented by formula CXX:

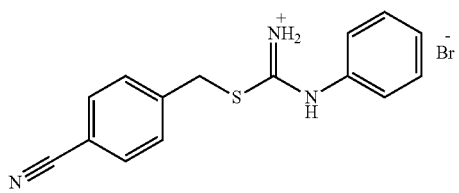 [SMILES: N#Cc1ccc(CSC(=N)Nc2ccccc2)cc1 ; Br]

or its analog, metabolite or prodrug and their combination thereof.

In another embodiment, the inhibitor used in the compositions and methods provided, comprises the structure represented by formula CXXI:

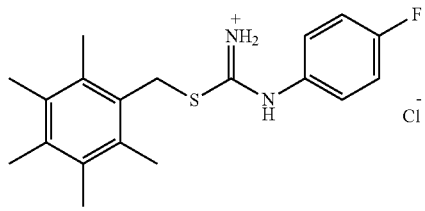 [SMILES: Cc1c(C)c(C)c(CSC(=N)Nc2ccc(F)cc2)c(C)c1C ; Cl]

or its analog, metabolite or prodrug and their combination thereof.

In another embodiment, the inhibitor used in the compositions and methods provided, comprises the structure represented by formula CXXII:

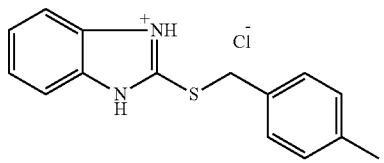 [SMILES: Cc1ccc(CSc2nc3ccccc3[nH]2)cc1 ; Cl]

or its analog, metabolite or prodrug and their combination thereof.

In another embodiment, the inhibitor used in the compositions and methods provided, comprises the structure represented by formula CXXIII:

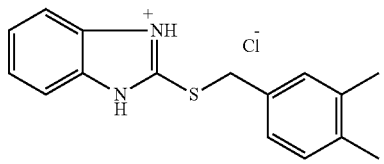 [SMILES: Cc1ccc(CSc2nc3ccccc3[nH]2)cc1C ; Cl]

or its analog, metabolite or prodrug and their combination thereof.

In another embodiment, the inhibitor used in the compositions and methods provided, comprises the structure represented by formula CXXIV:

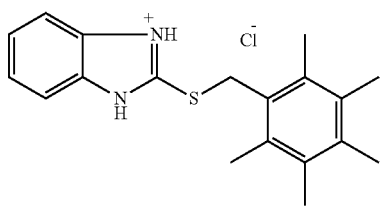 [SMILES: Cc1c(C)c(C)c(CSc2nc3ccccc3[nH]2)c(C)c1C ; Cl]

or its analog, metabolite or prodrug and their combination thereof.

In another embodiment, the inhibitor used in the compositions and methods provided, comprises the structure represented by formula CXXV:

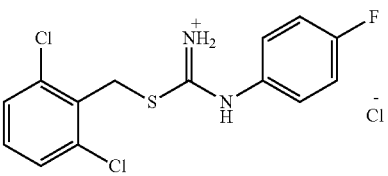 [SMILES: N=C(Nc1ccc(F)cc1)SCc1c(Cl)cccc1Cl ; Cl]

or its analog, metabolite or prodrug and their combination thereof.

In another embodiment, the inhibitor used in the compositions and methods provided, comprises the structure represented by formula CXXVI:

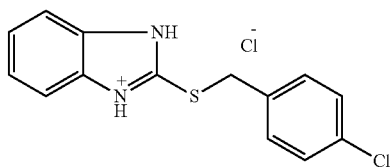 [SMILES: Clc1ccc(CSc2nc3ccccc3[nH]2)cc1 ; Cl]

or its analog, metabolite or prodrug and their combination thereof.

In another embodiment, the inhibitor used in the compositions and methods provided, comprises the structure represented by formula CXXVII:

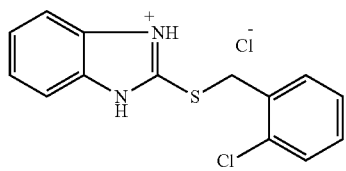 [SMILES: Clc1ccccc1CSc1nc2ccccc2[nH]1 ; Cl]

or its analog, metabolite or prodrug and their combination thereof.

In another embodiment, the inhibitor used in the compositions and methods provided, comprises the structure represented by formula CXXVIII:

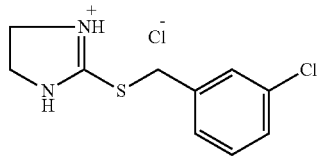 [SMILES: Clc1cccc(CSC2=NCCN2)c1 ; Cl]

or its analog, metabolite or prodrug and their combination thereof.

In another embodiment, the inhibitor used in the compositions and methods provided, comprises the structure represented by formula CXXIX:

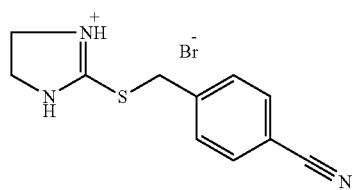 [SMILES: N#Cc1ccc(CSC2=NCCN2)cc1 ; Br]

or its analog, metabolite or prodrug and their combination thereof.

In another embodiment, the inhibitor used in the compositions and methods provided, comprises the structure represented by formula CXXX:

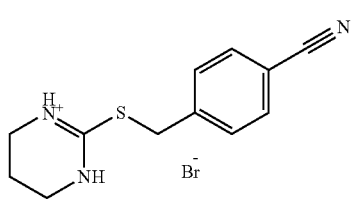

or its analog, metabolite or prodrug and their combination thereof.

In another embodiment, the inhibitor used in the compositions and methods provided, comprises the structure represented by formula CXXXI:

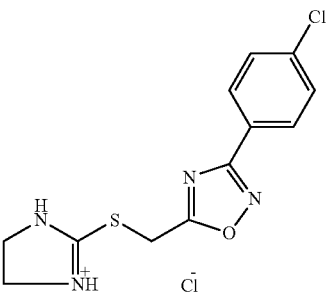 [SMILES: Clc1ccc(-c2noc(CSC3=NCCN3)n2)cc1 ; Cl]

or its analog, metabolite or prodrug and their combination thereof.

In another embodiment, the inhibitor used in the compositions and methods provided, comprises the structure represented by formula CXXXII:

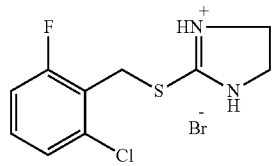

or its analog, metabolite or prodrug and their combination thereof.

In another embodiment, the inhibitor used in the compositions and methods provided, comprises the structure represented by formula CXXXIII:

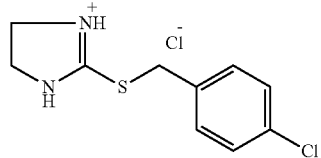 [SMILES: Clc1ccc(CSC2=NCCN2)cc1 ; Cl]

or its analog, metabolite or prodrug and their combination thereof.

In another embodiment, the inhibitor used in the compositions and methods provided, comprises the structure represented by formula CXXXIV:

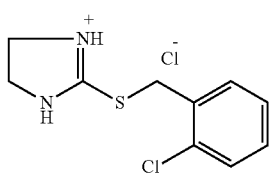 [SMILES: Clc1ccccc1CSC1=NCCN1 ; Cl]

or its analog, metabolite or prodrug and their combination thereof.

In another embodiment, the inhibitor used in the compositions and methods provided, comprises the structure represented by formula CXXXV:

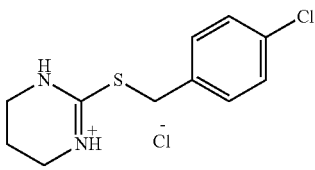 [SMILES: Clc1ccc(CSC2=NCCCN2)cc1 ; Cl]

or its analog, metabolite or prodrug and their combination thereof.

In another embodiment, the inhibitor used in the compositions and methods provided, comprises the structure represented by formula CXXXVI:

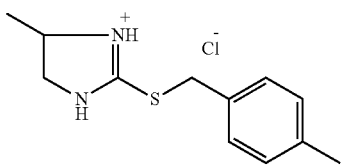

or its analog, metabolite or prodrug and their combination thereof.

In another embodiment, the inhibitor used in the compositions and methods provided, comprises the structure represented by formula CXXXVII:

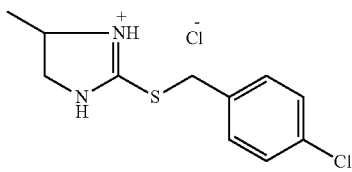

or its analog, metabolite or prodrug and their combination thereof.

In another embodiment, the inhibitor used in the compositions and methods provided, comprises the structure represented by formula CXXXVIII:

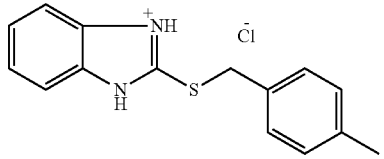 [SMILES: Cc1ccc(CSc2nc3ccccc3[nH]2)cc1 ; Cl]

or its analog, metabolite or prodrug and their combination thereof.

In another embodiment, the inhibitor used in the compositions and methods provided, comprises the structure represented by formula CXXXIX:

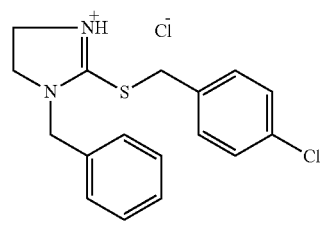 [SMILES: Clc1ccc(CSC2=NCCN2Cc2ccccc2)cc1 ; Cl]

or its analog, metabolite or prodrug and their combination thereof.

In another embodiment, the inhibitor used in the compositions and methods provided, comprises the structure represented by formula CXL:

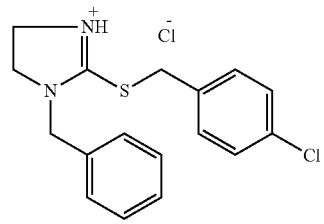 [SMILES: Clc1ccc(CSC2=NCCN2Cc2ccccc2)cc1 ; Cl]

or its analog, metabolite or prodrug and their combination thereof.

In another embodiment, provided herein is that an inhibitor provided herein inhibits the production of a pro-inflammatory cytokine. In another embodiment, provided herein is that an inhibitor provided herein inhibits the production of interleukin-2, interferon-gamma, or the combination thereof.

In another embodiment, provided herein is a composition comprising a selective c-Rel inhibitor that is any one of the structures represented by formulas I-CXL. In another embodiment, provided herein is a composition comprising a selective c-Rel DNA binding inhibitor having the structure of formula (I):

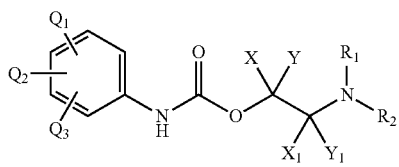

wherein $Q_1$, $Q_2$, $Q_3$ are independently H, halogen, $CF_3$, $OCH_2Ph$, O-alkyl, $OCF_3$, alkyl, or $Q_1$ and $Q_2$ form a saturated or unsaturated, substituted or un-substituted, carbocyclic or heterocyclic ring with the aniline ring; X and Y are independently H, alkyl, or form a saturated or unsaturated, substituted or un-substituted, carbocyclic or heterocyclic ring with N(R$_1$)(R$_2$). X$_1$ and Y$_1$ are independently H, alkyl, or X and Y form together a double bond, or form saturated or unsaturated, substituted or un-substituted, carbocyclic or heterocyclic ring with N(R$_1$)(R$_2$). R$_1$ and R$_2$ are independently H, NH$_2$, —N=alkyl, -alkyl, —CH(Ph)$_2$, substituted or un-substituted aryl, carbocyclic or heterocyclic aryl, substituted or un-substituted phenyl, C(O)-alkyl, or R$_1$ and R$_2$ form a saturated or unsaturated, substituted or un-substituted, carbocyclic or heterocyclic ring with the nitrogen atom;

or a selective c-Rel inhibitor having the structure of formula (II):

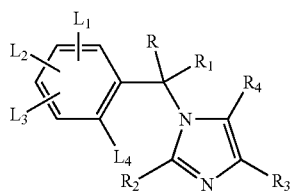

wherein L$_1$, L$_2$, L$_3$ and L$_4$ are independently H, halogen, alkyl, —NH$_2$, —COOAlkyl, —NO$_2$, pyrrolidine, —O-alkyl, or L$_1$ and L$_2$ form a saturated or unsaturated, substituted or un-substituted, carbocyclic or heterocyclic fused ring with the benzene ring; or L$_4$ together with R$_2$ forms a 6 membered fused ring with the imidazole and benzene rings; R and R$_1$ are independently H, NHCO-alkyl, or form together a double bond (=), or CO group (=O); R$_2$ is H, SH, OH, alkyl, -Ph-CF$_3$, —CH=C(Ph)-OC(O)-Ph, CH$_2$—S-Ph, CH$_2$—S-heterocyclic ring, CH$_2$OC(O)NH-Ph, —NHCH$_2$CH$_2$OH, -alkylene-OH, O-aryl, —O-alkyl, O—CH$_2$-Ph, O-phenyl, O-phenyl-alkyl, O-Ph-O-alkylene-Ph, —OCH$_2$Ph, —OCH$_2$CH=CH-Ph, —S-Phenyl, NH-alkyl, NH-phenyl, NH-aryl, —N(Me)-alkylene-phenyl, —NH-alkylene-phenyl, —NH-alkylene-OMe, —NH—N=CH-Ph, —NH—N—C(O)-alkyl, —NH-heterocyclic ring, NH-carbocyclic ring, —C(O)Ph, substituted or un-substituted, saturated or unsaturated hetrocyclic ring, substituted or un-substituted, saturated or unsaturated carbocyclic ring, or R$_2$ together with L$_4$ forms a 6 membered fused ring with the imidazole and benzene rings; R$_3$ is H, COO-alkyl, COOH, NO$_2$, substituted or un-substituted Ph, C(O)—N=NC(O)Ph or C(O)NH$_2$; and; R$_4$ is H, Ph, alkyl, NH$_2$, OH, Ph-OH or CH$_2$—OH;

or a selective c-Rel inhibitor having the structure of formula (CXIX):

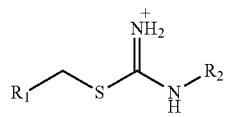

Wherein R$_1$ is a substituted phenyl or unsubstituted phenyl, whereby a substituted phenyl ring comprises CN, halogen, or alkyl substituent;

R$_2$ is

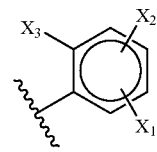

wherein X$_1$, X$_2$, or X$_3$ are independently H, halogen, alkyl, CN, COOH, or NH$_2$;

or X$_3$ forms with the =N$^+$H$_2$ a five membered fused ring; or R$_2$ forms with =N$^+$H$_2$ a five or six substituted or unsubstituted membered ring, whereby a five or six substituted membered ring comprises CH$_2$-Ph, aryl, or alkyl substituent.

In another embodiment, the present invention provides a composition comprising a selective c-Rel inhibitor having the structure of formula (III):

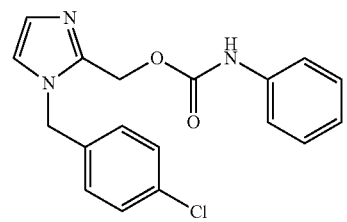 [SMILES: O=C(Nc1ccccc1)OCc1nccn1Cc1ccc(Cl)cc1]

or its analog, metabolite or prodrug and their combination thereof.

In another embodiment, provided herein is a composition comprising a selective c-Rel inhibitor having the structure of formula (IV):

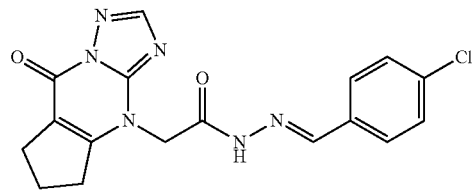 [SMILES: O=C(Cn1c2c(c(=O)n3ncnc13)CCC2)N/N=C/c1ccc(Cl)cc1]

or its analog, metabolite or prodrug and their combination thereof.

In another embodiment, provided herein is a composition comprising a selective c-Rel inhibitor having the structure of formula (V):

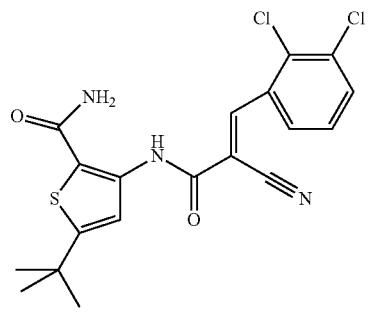 [SMILES: CC(C)(C)c1cc(NC(=O)/C(C#N)=C/c2cccc(Cl)c2Cl)c(C(N)=O)s1]

or its analog, metabolite or prodrug and their combination thereof.

In another embodiment, provided herein is a composition comprising a selective c-Rel inhibitor having the structure of formula (VII):

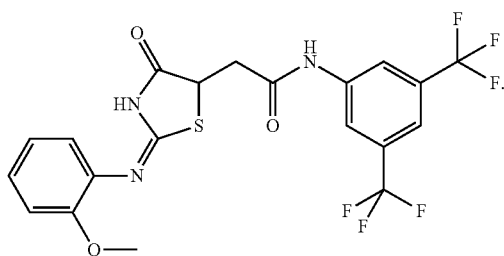 [SMILES: COc1ccccc1/N=C1\NC(=O)C(CC(=O)Nc2cc(C(F)(F)F)cc(C(F)(F)F)c2)S1]

In another embodiment, provided herein is a composition comprising any inhibitor as described hereinabove or its analog, metabolite or prodrug and their combination thereof. In another embodiment, provided herein is a composition comprising pharmaceutical excipients. In another embodiment, the compositions provided herein provide a positive clinical score for preventing multiple sclerosis. In another embodiment, the compositions provided herein provide a positive clinical score for preventing arthritis. In another embodiment, the compositions provided herein provide a positive clinical score for preventing rheumatoid arthritis. In another embodiment, the compositions provided herein provide a positive clinical score for preventing diabetes. In another embodiment, the compositions provided herein provide a positive clinical score for preventing Diabetes Melitus Type I. In another embodiment, the compositions provided herein provide a positive clinical score for preventing graft rejection. In another embodiment, the compositions provided herein provide a positive clinical score for preventing inflammation. In another embodiment, the compositions provided herein provide a positive clinical score for preventing neoplasma formation. In another embodiment, a positive clinical score comprises slight but clearly defined preventive effect for the above mentioned diseases.

In another embodiment, the compositions provided herein provide a positive clinical score for treating multiple sclerosis. In another embodiment, the compositions provided herein provide a positive clinical score for treating arthritis. In another embodiment, the compositions provided herein provide a positive clinical score for treating rheumatoid arthritis. In another embodiment, the compositions provided herein provide a positive clinical score for treating diabetes. In another embodiment, the compositions provided herein provide a positive clinical score for treating type 1 diabetes. In another embodiment, the compositions provided herein provide a positive clinical score for treating graft rejection. In another embodiment, the compositions provided herein provide a positive clinical score for treating inflammation. In another embodiment, the compositions provided herein provide a positive clinical score for treating neoplasma. In another embodiment, a positive clinical score comprises slight but clearly defined effect of treatment for the above mentioned diseases.

Pharmaceutical Compositions and Methods of Administration

The inhibitors used in the compositions and methods provided, and pharmaceutical compositions comprising same can be, in another embodiment, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment of methods and compositions used in the compositions and methods provided, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment used in the compositions and methods provided, the active ingredient is formulated in a capsule. In accordance with this embodiment, the compositions used in the compositions and methods provided, comprise, in addition to the active compound (e.g. the mimetic compound, peptide or nucleotide molecule) and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Topical formulations include, in another embodiment, gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active agent over a period of time.

In another embodiment, the active compound is delivered in a vesicle, e.g. a liposome. In other embodiments, carriers or diluents used in methods used in the compositions and methods provided, include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment used in the compositions and methods provided.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used. In another embodiment, polymeric materials are used; e.g. in microspheres in or an implant. In yet another embodiment, a controlled release system is placed in proximity to the target cell, thus requiring only a fraction of the systemic dose.

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Each of the above additives, excipients, formulations and methods of administration represents a separate embodiment used in the compositions and methods provided.

In one embodiment, the methods used in the compositions and methods provided, comprise administering an active compound as the sole active ingredient. However, also encompassed within the scope used in the compositions and methods provided, are methods for treating diseases and disorders that comprise administering the active compound in combination with one or more therapeutic agents. These agents include, but are not limited to, insulin agents, immunosuppressive agents, or drugs treating MS. In another embodiment, these agents are appropriate for the disease or disorder that is being treated, as is well known in the art.

In one embodiment, the methods used in the compositions and methods provided, comprise administering an active compound as the sole active ingredient. However, also encompassed within the scope used in the compositions and methods provided, are methods for treating diseases and disorders that comprise administering the active compound in combination with one or more therapeutic agents. These agents include, but are not limited to, insulin agents, immunosuppressive agents, or drugs treating MS. In another embodiment, these agents are appropriate for the disease or disorder that is being treated, as is well known in the art.

In one embodiment, the invention further provides a method of treating multiple sclerosis rejection in a subject comprising the step of contacting an inflammatory cell with a selective c-Rel DNA binding inhibitor. In one embodiment, the invention further provides a method of treating arthritis in a subject comprising the step of contacting an inflammatory cell with a selective c-Rel DNA binding inhibitor. In one embodiment, the invention further provides a method of treating diabetes rejection in a subject comprising the step of contacting an inflammatory cell with a selective c-Rel DNA binding inhibitor. In one embodiment, the invention further provides a method of treating graft rejection in a subject comprising the step of contacting an inflammatory cell with a selective c-Rel DNA binding inhibitor. In one embodiment, the invention provides that c-Rel DNA binding inhibitor masks the L1 cavity of a c-Rel protein, thereby treating or preventing multiple sclerosis, arthritis, diabetes, graft rejection, or a combination thereof in a subject.

In another embodiment, methods of treating diseases of the invention comprise contacting an inflammatory cell with an inhibitor of the invention. In another embodiment, methods of contacting an inflammatory cell with an inhibitor of the invention are known to one of skill in the art. In another embodiment, methods of contacting an inflammatory cell with an inhibitor of the invention comprise administering a composition comprising an inhibitor of the invention. In another embodiment, methods of contacting an inflammatory cell with an inhibitor of the invention comprise administering a composition which is targeted to a particular inflammatory cell.

In one embodiment, the invention further provides a method of preventing multiple sclerosis rejection in a subject comprising the step of contacting an inflammatory cell with a selective c-Rel DNA binding inhibitor. In one embodiment, the invention further provides a method of preventing arthritis in a subject comprising the step of contacting an inflammatory cell with a selective c-Rel DNA binding inhibitor. In one embodiment, the invention further provides a method of preventing diabetes rejection in a subject comprising the step of contacting an inflammatory cell with a selective c-Rel DNA binding inhibitor. In one embodiment, the invention further provides a method of preventing graft rejection in a subject comprising the step of contacting an inflammatory cell with a selective c-Rel DNA binding inhibitor. In one embodiment, the invention provides that c-Rel DNA binding inhibitor masks the L1 cavity of a c-Rel protein, thereby preventing multiple sclerosis, arthritis, diabetes, graft rejection, or a combination thereof in a subject.

In another embodiment, methods of preventing diseases of the invention comprise contacting an inflammatory cell with an inhibitor of the invention.

In one embodiment, the invention further provides a method of suppressing multiple sclerosis rejection in a subject comprising the step of contacting an inflammatory cell with a selective c-Rel DNA binding inhibitor. In one embodiment, the invention further provides a method of suppressing arthritis in a subject comprising the step of contacting an inflammatory cell with a selective c-Rel DNA binding inhibitor. In one embodiment, the invention further provides a method of suppressing diabetes rejection in a subject comprising the step of contacting an inflammatory cell with a selective c-Rel DNA binding inhibitor. In one embodiment, the invention further provides a method of suppressing graft rejection in a subject comprising the step of contacting an inflammatory cell with a selective c-Rel DNA binding inhibitor. In one embodiment, the invention provides that c-Rel DNA binding inhibitor masks the L1 cavity of a c-Rel protein, thereby suppressing multiple sclerosis, arthritis, diabetes, graft rejection, or a combination thereof in a subject.

In another embodiment, methods of suppressing diseases of the invention comprise contacting an inflammatory cell with an inhibitor of the invention.

In one embodiment, the invention further provides a method of reducing the symptoms associated with multiple sclerosis rejection in a subject comprising the step of contacting an inflammatory cell with a selective c-Rel DNA binding inhibitor. In one embodiment, the invention further provides a method of reducing the symptoms associated with arthritis in a subject comprising the step of contacting an inflammatory cell with a selective c-Rel DNA binding inhibitor. In one embodiment, the invention further provides a method of reducing the symptoms associated with diabetes rejection in a subject comprising the step of contacting an inflammatory cell with a selective c-Rel DNA binding inhibitor. In one embodiment, the invention further provides a method of reducing the symptoms associated with graft rejection in a subject comprising the step of contacting an inflammatory cell with a selective c-Rel DNA binding inhibitor. In one embodiment, the invention provides that c-Rel DNA binding inhibitor masks the L1 cavity of a c-Rel protein, thereby of reducing the symptoms associated with multiple sclerosis, arthritis, diabetes, graft rejection, or a combination thereof in a subject.

In another embodiment, methods of reducing the symptoms associated with diseases of the invention comprise contacting an inflammatory cell with an inhibitor of the invention.

In another embodiment, the invention further provides a method of identifying a selective c-Rel DNA binding inhibitor comprising the steps of: (a) constructing a c-Rel protein 3-D model; and (b) minimizing the model to identify a selective c-Rel DNA binding inhibitor, wherein the inhibitor interferes with L1 cavity thereby identifying a selective c-Rel DNA binding inhibitor.

In another embodiment, the invention provides that an inhibitor prevents Experimental Autoimmune Encephalomyelitis (EAE). In another embodiment, the invention provides that an inhibitor treats EAE. In another embodiment, the invention provides that an inhibitor as described herein prevents and treats EAE.

In another embodiment, provided herein is a kit comprising a reagent utilized in performing a method used in the compositions and methods provided. In another embodiment, provided herein is a kit comprising a composition, tool, or instrument used in the compositions and methods provided.

EXPERIMENTAL DETAILS SECTION

Materials and Experimental Methods

Example 1

Treatment of Human Inflammatory Diseases Using c-Rel Inhibitors

Experimental autoimmune encephalomyelitis (EAE) is an animal model for multiple sclerosis (MS). While the genetic and environmental factors that trigger MS vary, the common pathological outcome of the disease is the destruction of myelin-producing oligodendrocytes and their associated neuronal axons through a process called encephalomyelitis. Development of encephalomyelitis requires coordinated expression of a large number of genes that mediate the activation, migration and effector function of inflammatory cells (activated lymphoid and myeloid cells). These include genes that encode inflammatory cytokines, chemokines, and cytotoxic enzymes. Expression of these inflammatory genes is tightly regulated at the transcriptional level by specific transcription factors. Recent studies indicate that, c-Rel, the lymphoid member of the Rel/nuclear factor-κB (Rel/NF-κB) family, is a long sought-after transcriptional regulator of EAE. The mammalian Rel/NF-κB family consists of five members, each of which is endowed with a distinct set of function not shared by other members, although each member may also perform additional functions common to the family. Thus, unlike other members that are ubiquitously expressed, c-Rel is preferentially expressed by inflammatory cells, and is involved in regulating a special subset of immune responses. c-Rel-deficient mice do not suffer from developmental problems or infectious diseases, but are resistant to inflammatory diseases (despite the normal expression of other Rel/NF-κB proteins); c-Rel-deficient T cells are competent in survival and Th2 type responses but are severely compromised in their Th1 and Th17 type responses.

The Rel/NF-κB family of transcription factors represents one of the most attractive targets for anti-inflammatory therapy. Because Rel/NF-κB directly controls the expression of multiple inflammatory genes, its blockade is more effective for controlling inflammation than blocking one or a few downstream inflammatory genes or proteins. The first generation Rel/NF-κB drugs that block the entire Rel/NF-κB family have already been tested in both humans and animals. These include proteasome inhibitors (e.g., the FDA-approved PS-341), Rel/NF-κB decoy oligodeoxynucleotides and the NBD (nemo-binding domain) peptides, which are highly effective in preventing and treating models of autoimmune diseases including EAE. Additionally, glucocorticoids, which are currently used to control acute inflammation in MS patients, mediate their immunosuppressive effects, at least in part, through inhibiting Rel/NF-κB (glucocorticoids upregulate IkB expression and bind directly to Rel/NF-κB). However, because most Rel/NF-κB proteins are ubiquitously expressed and are involved in a variety of biological processes not related to autoimmunity, these drugs have significant side effects. Therefore, they can only be used for a short period of time to control acute inflammation.

This experimental section describes a new generation of drugs that are specific for c-Rel. Because c-Rel is expressed preferentially in inflammatory cells (activated lymphoid and myeloid cells) and is required for selected but not all immune responses, drugs targeting it should have significantly less side effects than drugs targeting the entire Rel/NF-κB family. As detailed below, new classes of c-Rel inhibitors have now been discovered that are effective in preventing and treating a inflammatory diseases.

The L1 Cavity of c-Rel and Novel Inhibitors that Target it.

c-Rel:DNA contacts are mediated by four loops, L1 and L2 loops from the N-terminal domain, and L3 and L4 loops from the C-terminal domain. DNA fragment is sandwiched between these loops. The contact residues are highly conserved across species, including human and mouse.

To design drugs that could disable human c-Rel binding to DNA (therefore blocking the biological activity of c-Rel), the chicken c-Rel 3-D model was humanized by replacing chicken residues with their human counterparts. The model was then minimized using the Insight II software (Accelrys, Inc). The minimized model was used to discover small molecule inhibitors that can interfere with the residues in loops L1 and L2. A small druggable cavity was identified using programs available in Insight II. This structure was designated as the L1 cavity. The L1 cavity is formed by loops L1, L2 and a helix. Residues Arg 21, Cys 26, Glu 27, Lys 110 and Lys 111 form the mouth of the L1 cavity (FIG. 2). A virtual screening approach was used to identify small molecule inhibitors. The inhibitors block the DNA binding to c-Rel by perturbing the key contact residues mentioned above.

R13 Blocks Cytokine Production by Inflammatory Cells

Figure 3:
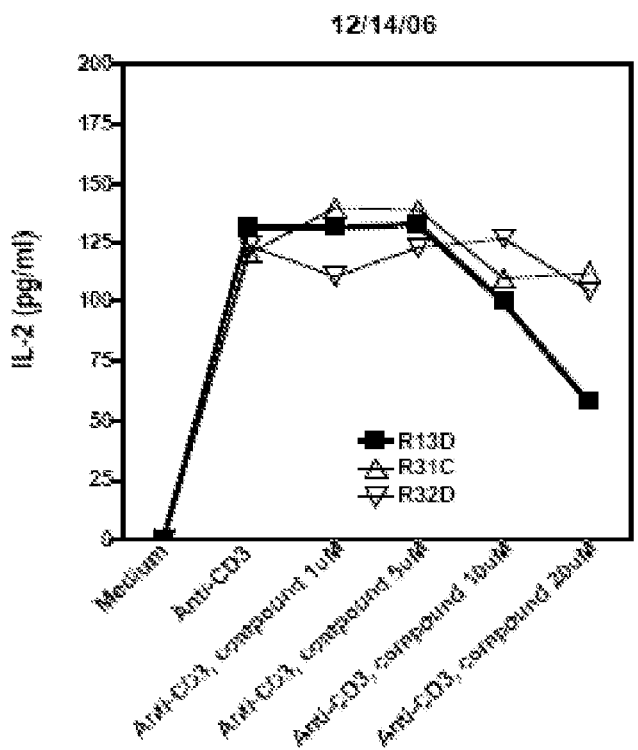
FIG. 3. Depicts a graph showing Splenocytes that were cultured under various conditions as indicated on the X-axis. Twenty-four hours later, cytokines in the supernatant were determined by ELISA (R13D is compound III, R31C. is compound IV, R32D is compound VII).
Figure 3:
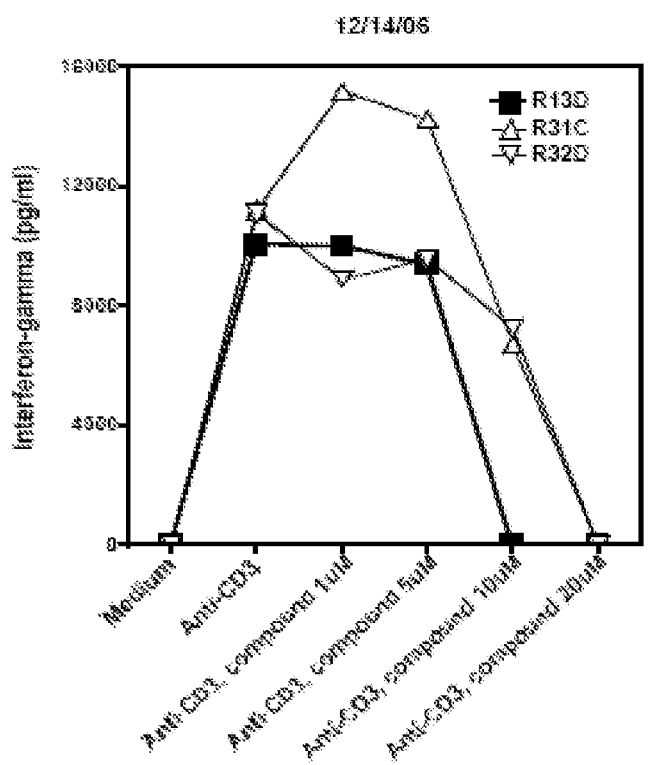

To determine whether these inhibitors are effective in suppressing cytokine production by inflammatory cells, spleen cells of B6 mice were treated with anti-CD3 antibody (to activate the inflammatory cells) with or without different concentrations of the compounds. As shown in FIG. 3, R13 significantly inhibited both Interleukin (IL)-2 and interferon-gamma production while the other two compounds had an effect only on interferon-gamma. The proliferation was not significantly affected by these compounds suggesting that they are not toxic to cells. As further shown in FIG. 1 IL-2 and IFN-gamma were inhibited by compound II, compound V, and compound VI at concentrations ranging from 5-20 μM.

R13 is Effective in Both Preventing and Treating EAE

Figure 5:
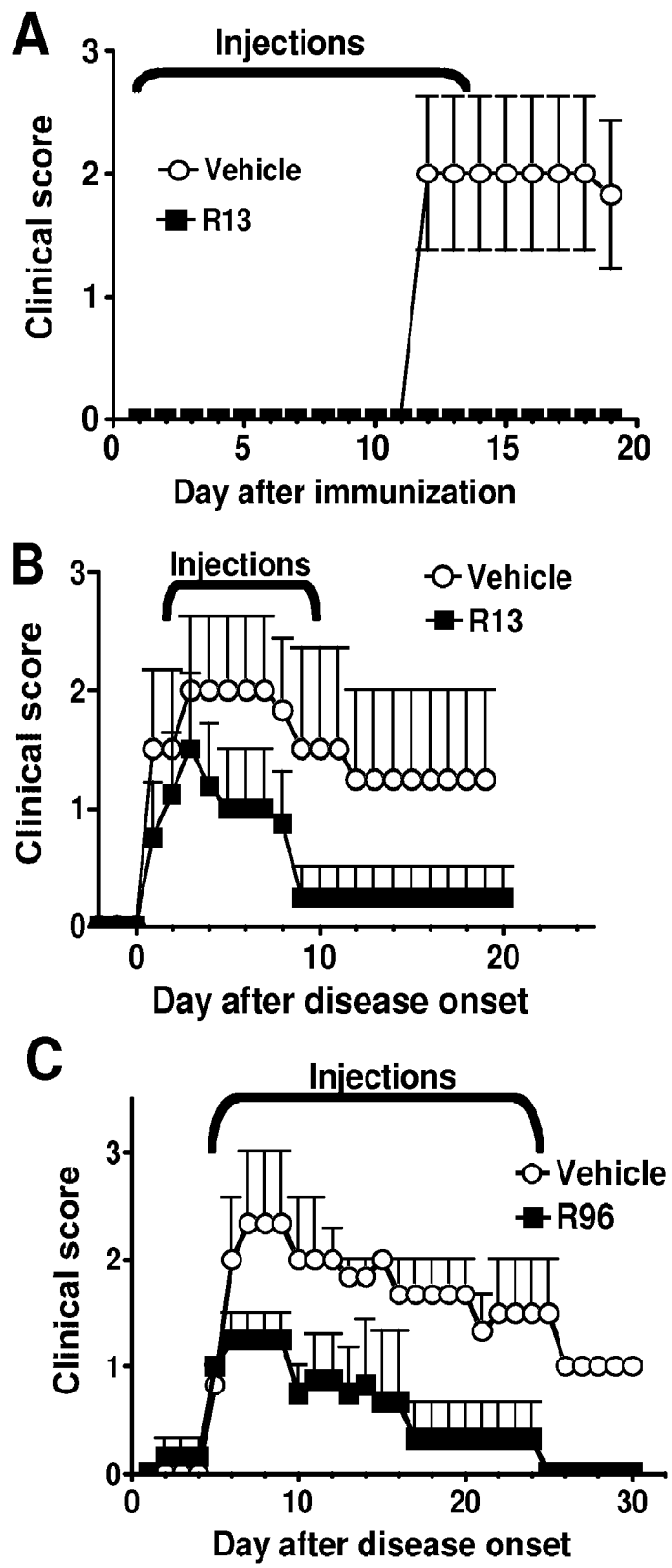
FIG. 5 shows prevention and treatment of EAE using c-Rel blockers. C57BL/6 mice, 6-8 per group, were immunized to induce EAE with MOG38-50 peptide. A) Mice were injected i.p. with vehicle or 100 ug/mouse/injection of R13 daily from day 1 to day 13. B) Mice were injected i.p. with vehicle or 100 ug/mouse/injection of R13 daily from day 2 (after onset) to day 10. C) Mice were injected i.p. with vehicle or 100 ug/mouse/injection of R96 daily from day 5 (after onset) to day 24. The differences between the two groups are statistically significant as determined by Mann-Whitney U test (p<0.001) for a after day 12, for B after day 9 and for C after day 8. Results are representative of 3 experiments.

To determine the effect of R13 on EAE, the drug (inhibitor) was injected either before or after the onset of the disease. As shown in FIG. 5, R13D (compound III) is effective in both preventing and treating EAE.

Example 2

Identification of c-Rel Blockers by Structure-Based Drug Design (SBDD)

The three-dimensional structure of chicken c-Rel bound to DNA has been determined (See e.g. Example 1). The structural studies show that c-Rel:DNA contacts are mediated by four loops, L1 and L2 loops from the N-terminal domain, and L3 and L4 loops from the C-terminal domain. DNA fragment is sandwiched between these loops. The contact residues are highly conserved across species, including chicken, human and mouse.

To design drugs that could disable human c-Rel binding to DNA (therefore blocking the biological activity of c-Rel), chicken c-Rel 3-D model was first humanized by replacing chicken residues with their human counterparts. The model was then minimized using the Insight II software (Accelrys, Inc). The minimized model was used to discover small molecule inhibitors that can interfere with the residues in loops L1 and L2. A small druggable cavity was identified using programs available in Insight II. This structure was designated as the L1 cavity. The L1 cavity is formed by loops L1, L2 and a helix. Residues Arg 21, Cys 26, Glu 27, Lys 110 and Lys 111 form the mouth of the L1 cavity (FIG. 2). A virtual screening approach was used to identify small molecule inhibitors that block DNA binding to the L1 cavity by perturbing these key contact residues as we previously described. From ~50,000 drug-like molecules of available chemical libraries, about 100 hits were identified. Secondary screening using an IL-2 release assay (described hereinbelow) led to the identification of 10 compounds that significantly inhibited IL-2 production by T cells. These compounds fall into two structural classes, the phenylcarbamates (FIG. 2C) and sulfanyl-methaniminium-based compounds, represented by R13:

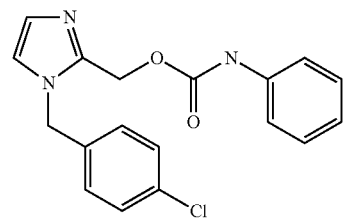 [SMILES: O=C(Nc1ccccc1)OCc1nccn1Cc1ccc(Cl)cc1]

and R96 (the most potent compounds),

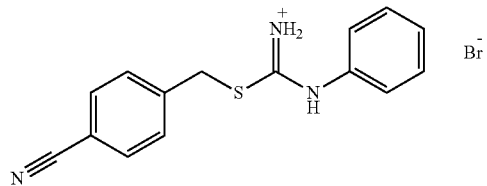 [SMILES: N#Cc1ccc(CSC(=N)Nc2ccccc2)cc1 ; Br]

respectively. The SBDD studies were conducted at the University of Pennsylvania.

Figure 4:
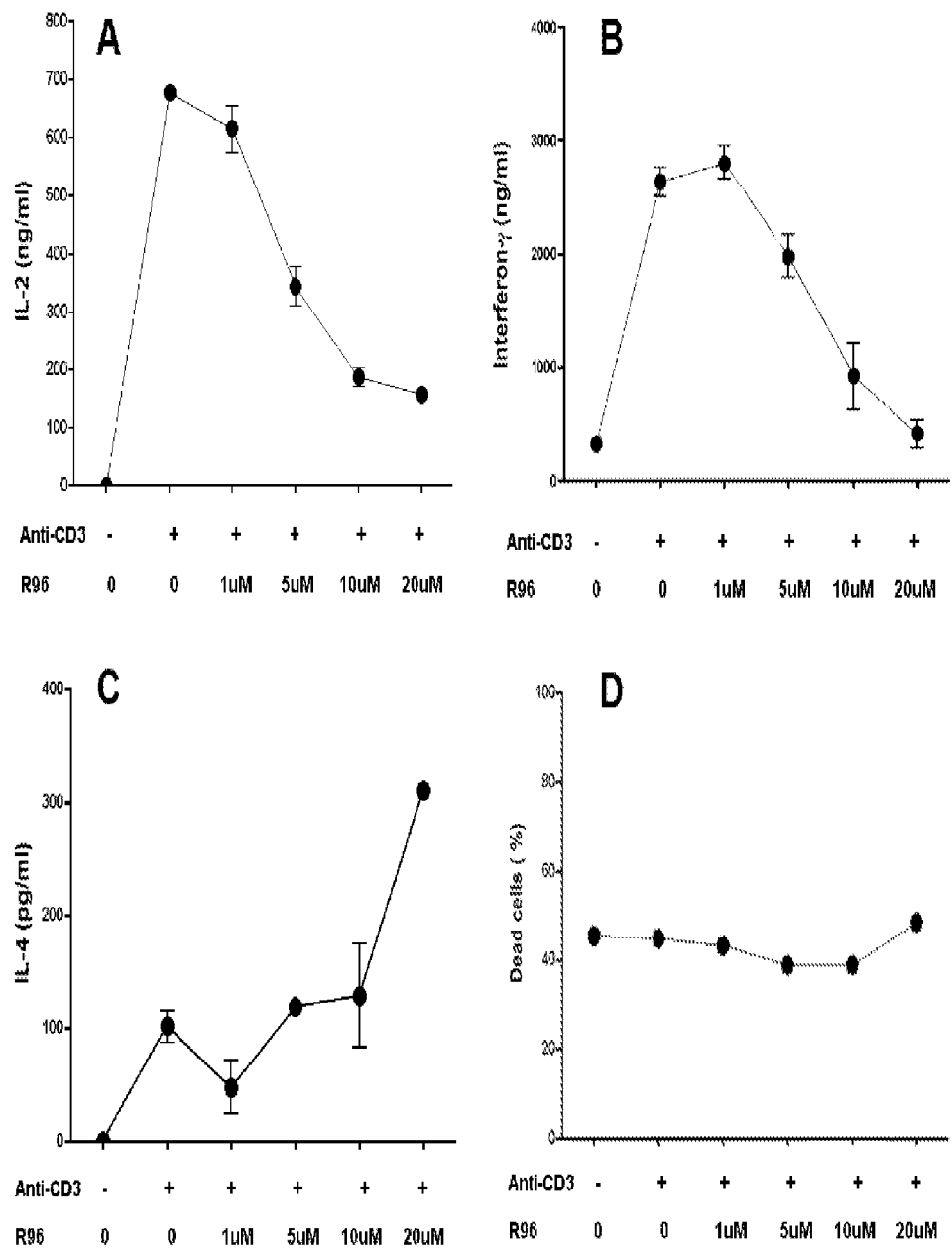
FIG. 4 depicts graphs of the results from C57BL/6 mice that were immunized to induce EAE with 1) is a subcutaneous injection on flanks of 300 µg MOG38-50 peptide in 0.1 ml PBS emulsified in an equal volume of complete Freund's adjuvant containing 500 µg mycobacterium tuberculosis H37RA, and 2) is an intravenous injection of 100 ng pertussis toxin in 0.1 ml PBS. A second injection of pertussis toxin (200 ng per mouse) was given 48 h later. For FIG. 4A, mice were injected with 100 ug R13D (compound III) daily from day 1 to day 13. For FIG. 4B, mice were injected with 100 ug R13D (compound III) daily from day 25 (after onset) to day 32. Mice were examined daily for signs of EAE and scored as follows (6). 0—no disease; 1—tail paralysis; 2—hind limb weakness; 3—hind limb paralysis; 4—hind limb plus forelimb paralysis; 5—moribund or dead. The differences for all the parameters between c-Rel$^{+/+}$ and c-Rel$^{-/-}$ mice are statistically significant (p<0.001). The experiment was repeated twice with similar results.

Example 3 c-Rel Blockers Selectively Regulate Cytokine Production but not Survival of T Cells To determine whether the c-Rel blockers identified above are effective in regulating inflammatory cell function, splenocytes or purified CD4+ splenic T cells of C57BU6 mice were treated with anti-CD3 and anti-CD28 in the presence of increasing concentrations of the compounds. Cytokine expression was determined by ELISA, flow cytometry or real-time PCR, whereas CD4 expression and cell survival were determined by flow cytometry alone. Of 15 compounds tested to date, including 5 from FP-HTS and 10 from SBDD, at least 10 significantly inhibited IL-2, IL-6, IL-17A, L-21 and/or IFN-g expression but not that of IL-4 and CD4 (which are not c-Rel targets). Eight of these compounds showed no detectable cytotoxicity to either resting or activated splenocytes in the culture. A representative of these compounds, i.e., R96 identified from SBDD, is shown in FIG. 4. The $IC_{50}$ of R96 for IL-2 inhibition is ~5 mM. Even at the highest concentration tested (20 mM), R96 does not significantly affect the survival of CD4+ T cells or total splenocytes. Because Th1 cytokine IFN-g inhibits the activity of Th2 cells, the increased IL-4 in cultures containing 20 mM R96 could be due to the reduced IFN-g in the culture. Of note is that although an increase in IL-4 was also observed in c-Rel-deficient T cells in the culture, c-Rel-deficient mice do not develop heightened humoral immunity or hypersensitivity because c-Rel-deficiency also hinders B cell activation and antibody production. In fact, c-Rel-deficient mice have reduced but not increased IgG1, IgG3 and IgE production.

Example 4 c-Rel Blockers are Effective in Both Preventing and Treating EAE

To determine the effect of c-Rel blockers on EAE, two lead compounds were tested, R13 and R96, in both prophylaxis and treatment regimens. For prophylaxis (which may be used to prevent MS relapses during remission), the compounds were injected intraperitoneally (i.p.) once a day for a total of 13 days starting from the day of immunization. The amount of the compound used (100 mg/mouse/injection) was selected based on the $IC_{50}$ of the compound and the total volume of the mice (~20 ml), so that the theoretical maximal mean concentration of the compound in the whole animal is more than $IC_{50}$ of the compound. The vehicle used to dissolve the compound was PBS. Remarkably, injection of the c-Rel blockers completely prevented the development of EAE in all mice (FIG. 5A). To evaluate the disease pathology and anti-myelin autoimmunity, mice were sacrificed 20 days after immunization and tested as was previously described. As expected, anti-MOG Th1 (IL-2 and IFN-g) and Th17 (IL-17A) responses were significantly reduced in mice treated with the c-Rel blocker. IL-4 was not detected in splenocyte cultures of either group. Encephalomyelitis, characterized by leukocyte infiltration of the white matter of brain and spinal cord was evident in control but not c-Rel blocker-treated mice. These results are similar to those shown previously for c-Rel-deficient mice, indicating that blocking c-Rel alone is sufficient to prevent EAE.

However, prophylaxis alone is not sufficient for controlling MS, because most patients seek clinical care after the onset of the disease. To determine the effectiveness of c-Rel blockers in treating ongoing EAE, the c-Rel blockers were injected into mice after the onset of the disease. Both R13 and R96 were found to significantly ameliorated the symptoms of ongoing EAE (FIG. 5B, 5C). For example, the mean disease scores of mice before the treatment were ~1.0 in both groups (FIG. 5C). Seven days into the treatment, the disease scores increased to 1.83±0.16 in the control group but decreased to 0.75±0.43 in the R96-treated group (p<0.001). Histological examination performed at the end the experiment supported the clinical findings, with the c-Rel blocker-treated group showed significantly reduced degree of encephalomyelitis. Thus, c-Rel blockers are effective in suppressing EAE after its onset.

Example 5

Synthesis of 096

The retrosynthetic analysis for the preparation of C-rel inhibitor 096 is outlined in Scheme 1:

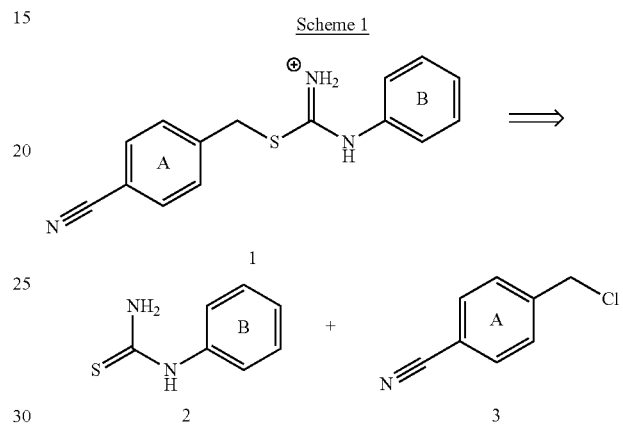

Reaction of N-phenylthiourea 2 and benzyl chloride 3[1] leads to the formation of 1. As shown in Scheme 2:

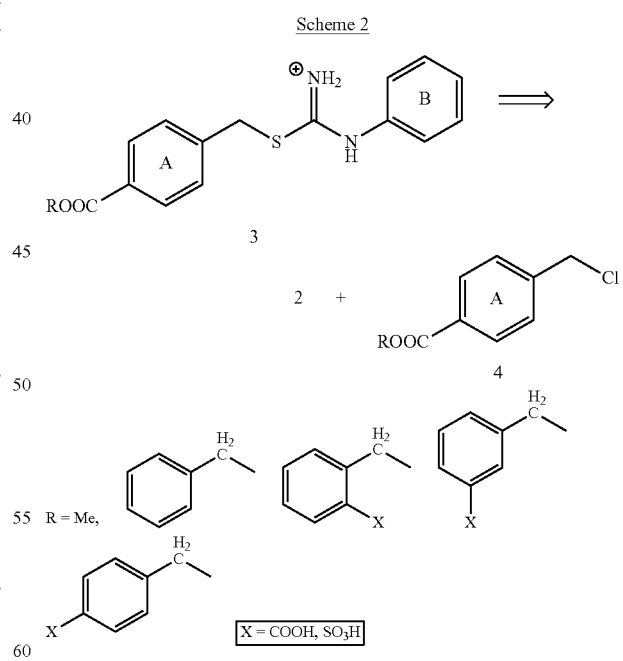

The preparation of 3 is achieved by reaction of 2 with 4, which leads to eight (8) novel analogs based on the nature of the ester R group as indicated in Scheme 2 (eight new compounds, including methyl ester, benzyl ester, and 3-substituted benzyl esters, substituted with carboxylate and sulfonate, respectively, are prepared).

Also examined is the use of amido functionalities, starting from 6 as shown in 5 (Scheme 3), in lieu of the carboxyl group in 3. Using the same R groups indicated in Scheme 2, it should be possible to prepare eight (8) additional amide-containing analogs.

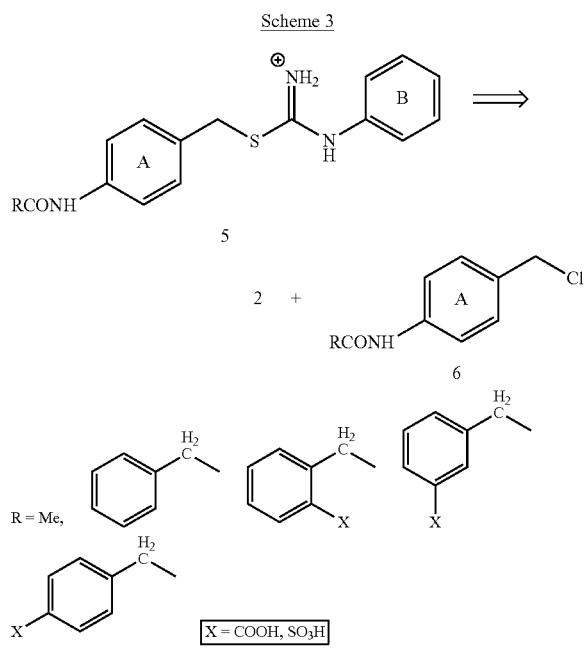

The aromatic ring 3 are expanded to occupy a larger conformational space in the binding pocket shown in FIG. 2. Substitution of the A ring of 1 (Scheme 1) with α- and β-naphthylmethyl, 7 and 9, respectively, is shown in Scheme 4 and require the substitution of the commercially available α- and β-naphthylmethylchlorides 8 and 10 for 3. In each case, the substitution of the naphthyl rings of 8 and 10 with negatively charged groups, such as carboxylate, sulfonate, and also a tetrazole, is carried out so that eight (8) additional analogs are prepared in the expanded aryl series.

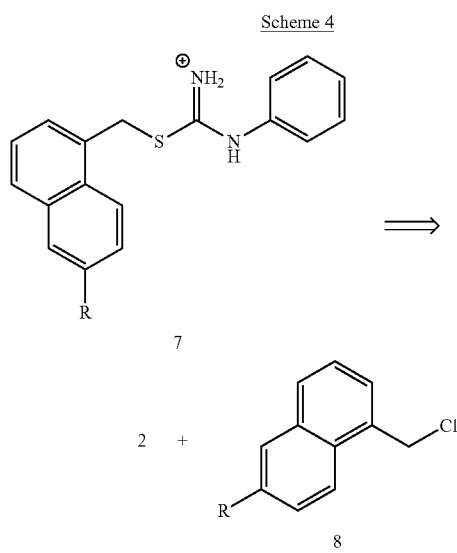

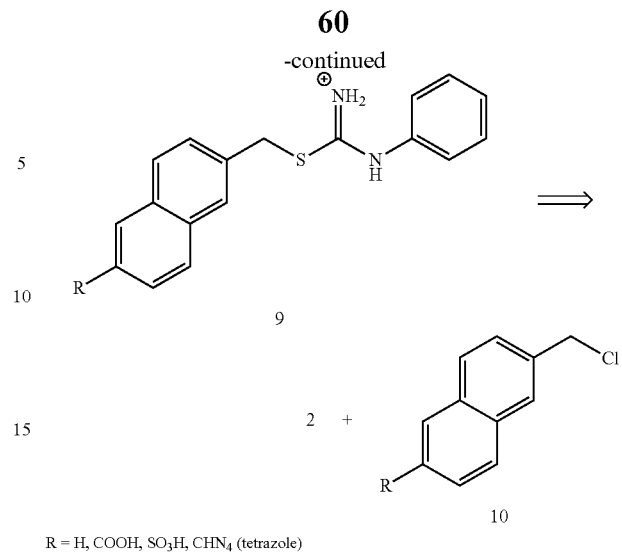

$R = H, COOH, SO_3H, CHN_4$ (tetrazole)

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of treating, inhibiting or suppressing, or meliorating symptoms associated with multiple sclerosis, arthritis, diabetes, graft rejection, or a combination thereof in a subject, comprising the step of contacting the subject with a composition comprising a selective c-Rel:DNA binding inhibitor wherein said c-Rel DNA binding inhibitor masks the L1 cavity of the c-Rel protein, thereby treating, inhibiting or suppressing, or ameliorating symptoms associated with inflammatory conditions that are multiple sclerosis, arthritis, diabetes, colitis, lupus, autoimmunity, graft rejection, or a combination thereof in the subject, wherein said composition comprises a compound set forth by the structure of formula (CXIX):

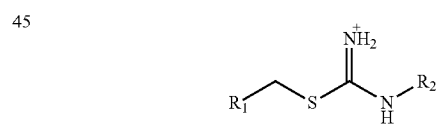

wherein $R_1$ is substituted phenyl or unsubstituted phenyl; $R_2$ is

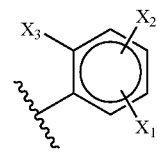

wherein $X_1$, $X_2$, or $X_3$ are independently H, halogen, alkyl, CN, COOH, or $NH_2$;
or $X_3$ forms with the $=N^+H_2$ a five membered fused ring; or
$R_2$ forms with $=N^+H_2$ a five or six substituted or unsubstituted membered ring, or their combination.

2. The method of claim 1, whereby the inhibitor further inhibits the production of interleukin-2, interferon-gamma, or both.

3. The method of claim 1, whereby said L1 cavity comprises amino acids; Arg 21, Cys 26, Glu 27, Lys 110, and Lys 111.

* * * * *